United States Patent
Selvarajan et al.

(10) Patent No.: US 8,844,529 B2
(45) Date of Patent: Sep. 30, 2014

(54) VENTLESS MASK CPAP SYSTEM

(75) Inventors: Karthikeyan Selvarajan, Gosford (AU); Philip Rodney Kwok, Chatswood (AU); Barton John Kenyon, Ashfield (AU); Bruce David Gregory, Leichardt (AU); Nicholas Jerome Reed, Mount Colah (AU); Christopher Kingsley Blunsden, Newport Beach (AU)

(73) Assignee: ResMed Limited, Bella Vista (AU)

( * ) Notice: Subject to any disclaimer, the term of this patent is extended or adjusted under 35 U.S.C. 154(b) by 1816 days.

(21) Appl. No.: 11/887,547

(22) PCT Filed: Mar. 29, 2006

(86) PCT No.: PCT/AU2006/000417
§ 371 (c)(1),
(2), (4) Date: Dec. 28, 2009

(87) PCT Pub. No.: WO2006/102707
PCT Pub. Date: Oct. 5, 2006

(65) Prior Publication Data
US 2010/0147302 A1    Jun. 17, 2010

Related U.S. Application Data

(60) Provisional application No. 60/667,052, filed on Apr. 1, 2005, provisional application No. 60/706,430, filed on Aug. 9, 2005, provisional application No. 60/775,334, filed on Feb. 22, 2006.

(51) Int. Cl.
*A61M 16/06* (2006.01)
*A61M 16/00* (2006.01)

(52) U.S. Cl.
CPC ........... *A61M 16/06* (2013.01); *A61M 16/0009* (2014.01); *A61M 2016/0039* (2013.01); *A61M 16/00* (2013.01); *A61M 2016/0027* (2013.01); *A61M 2206/14* (2013.01); *A61M 16/0066* (2013.01); *A61M 2230/432* (2013.01); *A61M 16/0633* (2014.01)
USPC ..................................................... 128/205.19

(58) Field of Classification Search
USPC ............. 128/204.18, 205.19, 205.25, 206.21, 128/207.13, 207.18
See application file for complete search history.

(56) References Cited

U.S. PATENT DOCUMENTS

| 4,248,218 A * | 2/1981 | Fischer | 128/204.18 |
| 4,944,310 A * | 7/1990 | Sullivan | 128/848 |

(Continued)

FOREIGN PATENT DOCUMENTS

| DE | 199 54 724 A1 | 6/2001 |
| EP | 1459779 | 9/2004 |

(Continued)

OTHER PUBLICATIONS

International Preliminary Report on Patentability, Appln. No. PCT/AU2006/000417 (Oct. 3, 2007), 8 pgs.

(Continued)

*Primary Examiner* — Laura Bouchelle
(74) *Attorney, Agent, or Firm* — Nixon & Vanderhye, P.C.

(57) ABSTRACT

A CPAP or other ventilation system includes a mask, a flow generator, a positive or high pressure line to provide positive or high pressure air from the flow generator to the mask and a vacuum or return line provided to actively extract exhaled gas from the breathing chamber and/or the air delivery conduit of the mask. The vacuum or return line includes a vent outlet preferably positioned remote from the mask.

34 Claims, 13 Drawing Sheets

(56) References Cited

U.S. PATENT DOCUMENTS

| | | | |
|---|---|---|---|
| 5,419,317 A | | 5/1995 | Blasdell et al. |
| 6,131,571 A | * | 10/2000 | Lampotang et al. ..... 128/204.21 |
| 6,182,656 B1 | * | 2/2001 | Sagiv ........................ 128/204.18 |
| 6,345,619 B1 | | 2/2002 | Finn |
| 6,561,190 B1 | | 5/2003 | Kwok |
| 6,561,191 B1 | | 5/2003 | Kwok |
| 6,581,594 B1 | | 6/2003 | Drew et al. |
| 6,691,707 B1 | | 2/2004 | Gunaratnam et al. |
| 6,736,140 B1 | * | 5/2004 | Baczkowski ............. 128/206.21 |
| 6,910,483 B2 | | 6/2005 | Daly et al. |
| 7,011,090 B2 | | 3/2006 | Drew et al. |
| 2001/0032648 A1 | | 10/2001 | Jestrabek-Hart |
| 2004/0069306 A1 | | 4/2004 | Moenning et al. |
| 2004/0094157 A1 | | 5/2004 | Dantanarayana et al. |
| 2005/0103339 A1 | | 5/2005 | Daly et al. |
| 2005/0145247 A1 | | 7/2005 | Nashed |

FOREIGN PATENT DOCUMENTS

| | | |
|---|---|---|
| FR | 2827778 | 1/2003 |
| SU | 468626 | 10/1975 |
| SU | 468626 | 4/1977 |
| WO | 92/11054 | 7/1992 |
| WO | 97/00092 | 1/1997 |
| WO | WO 97/00092 | 1/1997 |
| WO | 2005/097247 | 10/2005 |

OTHER PUBLICATIONS

EP Extended Search Report filed in EP Appln. No. 06721299.3 (Jan. 27, 2010).

International Search Report for PCT/AU2006/000417 mailed May 24, 2006.

* cited by examiner

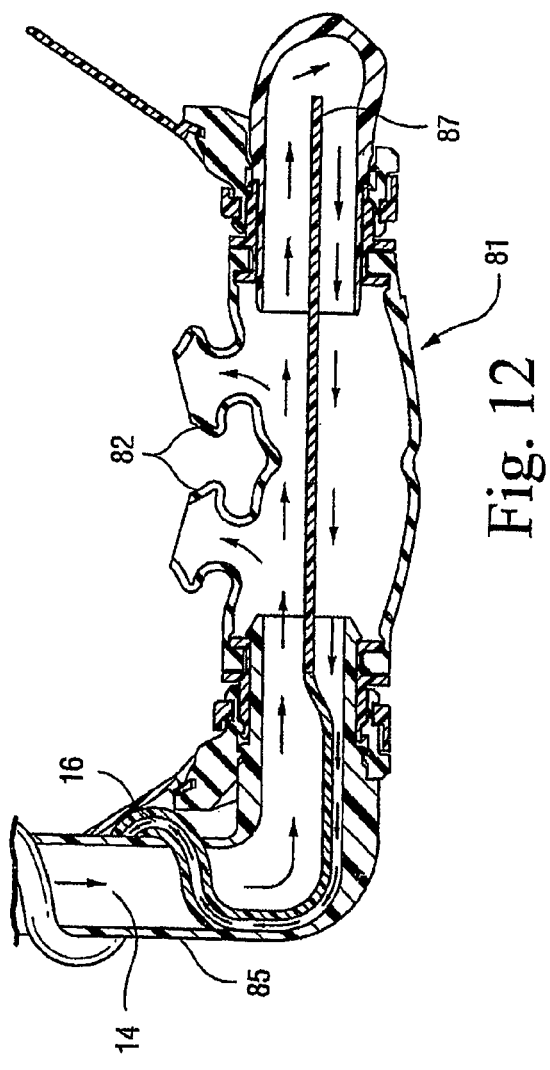
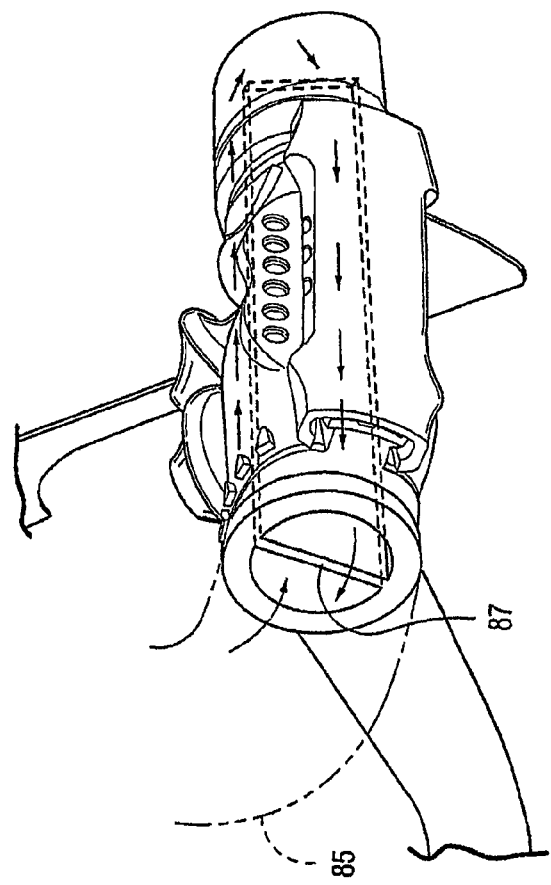

VENTLESS MASK CPAP SYSTEM

CROSS-REFERENCE TO RELATED APPLICATIONS

This application is the U.S. national phase of International Application No. PCT/AU2006/000417, filed Mar. 29, 2006, which designated the U.S. and claims priority to Provisional Application Nos. 60/667,052, filed Apr. 1, 2005, 60/706,430, filed Aug. 9, 2005, and 60/775,334, filed Feb. 22, 2006, each incorporated by reference in its entirety.

STATEMENT REGARDING FEDERALLY SPONSORED RESEARCH OR DEVELOPMENT

N/A

BACKGROUND OF THE INVENTION

The primary non-invasive method of treating Obstructive Sleep Apnea (OSA) has traditionally used a Continuous Positive Airway Pressure (CPAP) device (also generically known as a Flow Generator), an interface to the patient's airway, and an interconnecting tube or pipe to supply a gas. There have also been further variations to this system including a flow generator that is integrated with a mask interface without an interconnecting tube (see U.S. Provisional Application No. 60/505,718 filed Sep. 25, 2003, and International Application No. PCT/AU04/01309, filed Sep. 27, 2004, each incorporated herein by reference in its entirety.

Traditional mask interfaces are configured to incorporate several fundamental features. They usually embody a frame, a sealing cushion, and headgear to secure the assembly to a patient's head, an inlet pipe for tubing attachment, and a vent that is usually part of a mask frame of elbow attached to the mask frame.

The mask vent for a CPAP mask allows a constant biased flow of gas from within the mask interface (gas exhalation region of a patient) to atmosphere (region external to a mask interface surrounding the patient). This constant or variable flow of air allows the partial pressure of waste exhaust gas from a patient's lungs (Carbon Dioxide or $CO_2$), to be flushed to the atmosphere to prevent undesirable $CO_2$ rebreathing or suffocation.

Mask vents have constantly proved to be a complex design issue for engineers who are required to develop vents that are quiet for patients and bed partners, flush out adequate $CO_2$, and do not 'jet' irritating streams of air onto the body or bed partner due to poor dissipation or vented air direction.

The mask interface's vent flows outwards through one or a plurality of holes integrated within a mask interface that is in direct communication with the breathing gas chamber (inside of the mask frame). This occurs because there is a greater pressure inside the mask than the surrounding atmosphere. This is the basic principle of CPAP therapy, which raises the pressure within the patient's airways compared to the surrounding atmosphere.

The flow of fluid (air) can be explained by simple physics. A wall with a through-hole communicating with both sides (of the wall) with a higher pressure on one side will generally cause the air to flow towards the lower pressure side.

All existing CPAP masks have vented their patient-expired gases in the vicinity of the patient's head. The vent is either located on the mask frame or otherwise integrated into an attached component such as a rotating elbow, which is subsequently attached to the mask frame. See also U.S. Patent Publication No. 2001/0032648 A1

This traditional vent location has provided an ideal location for $CO_2$ washout but poor location for noise as it is relatively close to the patient's ears.

Carbon Dioxide Washout and Rebreathing

In general, greater flow through the vent holes will decrease $CO_2$ rebreathing at a given pressure, as there is increased washout of expired gas. An undesirable effect typically results with increased vent flow, that is vent noise.

Adequate venting is generally a design issue at lower treatment pressures (say 4 cm water) where $CO_2$ rebreathing is more likely. At higher pressures, the vent flow generally increases well beyond the safe limits required to prevent rebreathing, therefore the vent flow at high pressures may be mechanically and/or electrically reduced by variable vents and still maintain effective $CO_2$ washout.

Vents have been designed to reduce the flow at higher treatment pressures, which may also provide reduced noise due to reduced vent flow. These variable vent valves, as some may describe in the art, are typically used to reduce the power required by a flow generator to deliver treatment pressures at the higher pressure ranges. One such variable vent example is known as the Respironics Plateau Valve. Other examples are ResMed's U.S. Non-Provisional application Ser. No. 10/433,980, filed Nov. 10, 2003, and ResMed's U.S. Provisional Application No. 60/640,184 filed Dec. 30, 2004, each incorporated herein by reference in its entirety. These vents, though lower in vent flow, are still an irritating noise source near the patient's (and bed partner's) ears.

Invasive ventilation is generally applied through the trachea and is often used where a patient is seriously ill and cannot effectively breathe on their own.

In Non-Invasive Positive Pressure Ventilation (also known as NiPPV or NPPV), a bi-level positive pressure device can be connected to the patient via a non-vented mask interface. These ventilators allow various modes of mechanical ventilation ranging from assisted breathing to fully controlled ventilation. In some cases, the machine can be set so that a patient can breathe almost naturally, receiving occasional air pressure to assist with individual breaths and has been known as assisted ventilation.

In sicker patients, the degree of ventilator driven respiration can be increased, and if necessary, the ventilator can take over the work of breathing entirely and has been known as Controlled Ventilation.

The expired air usually results from the patient's lungs deflating due to the wall elasticity after having been actively inflated by the machine. The gas outlet tube that is attached at one end to the mask interface is usually open at the other to atmosphere and works in similar fashion to a typical mask vent, where the machine incoming positive gas pressure 'pushes' the exhaust gas out from the patient interface. For example, the pressure within the mask pushes the exhausted air down a secondary tube that is controllable via a valving arrangement to detect exhalation of the patient and then vent the exhaled gas to either the ventilator or atmosphere.

Ventilators (as described above) differ from CPAP therapy. In CPAP, only sufficient gas flow to achieve adequate washout of $CO_2$ needs to be vented to atmosphere. The patient does most of the work of breathing, not the device. The $CO_2$ only represents a small partial pressure of the overall volume of air that is expired from a patient, therefore only a relatively small flow of air (for example 40-60 liters of intentional leak per minute at 20 cm of delivered pressure in the mask) is required to wash out adequate levels of $CO_2$.

ResMed engineers have also shown that the gas flow dynamics inside a mask system have a significant effect on $CO_2$ rebreathing, not only physical dead space as was previously understood. Moreover, the vent hole location and also designing a defined or biased flow of air (see ResMed's U.S. patent application Ser. No. 10/655,621, filed Sep. 5, 2003, incorporated by reference in its entirety, and commercially embodied in ResMed's Activa™ mask) reduces $CO_2$ further. Designing a mask system to meet this requirement represents a significant design challenge with many tradeoffs such as noise and vented direction (and air jetting). The complexity of the mask design may also affect maintenance such as ease of cleaning and may negatively influence the mask configuration and appearance.

Mask interface internal dead space (the physical internal volume of the mask adjacent to but external to the patient's airways) also affects the $CO_2$ rebreathing. Generally, increased volume results in increased rebreathing. The vent design, the location relative to the mask and patient airways, and impedance through the holes all affect rebreathing performance. A significant development effort is therefore required before a mask interface can be marketed and safely used on a patient.

Noise

Sleep apnea is a medical disorder that has been successfully treated globally using the non-invasive method known as CPAP. As the device is expected to operate in a home or hospital environment where patients and their bed partners are expected to sleep, it is a fundamental need for the treatment system to be quiet during use to minimize disturbance, irritation and discomfort.

Noise generally occurs as a flow of air through the vent(s) becomes turbulent and/or interferes with an object before dissipating to the atmosphere. Two main methods are employed by most manufacturers to reduce noise. Namely, producing vents that flow in a laminar state (smooth flow), and those that dissipate the vented gas. Laminar state vents generally attempt to smooth the flow of air as it exits a mask interface. In dissipation, the vented gas is passed through many tiny air passages to absorb sound energy.

Noise of vented air can be reduced using a multitude of methods. For example, many small holes can reduce noise as claimed in ResMed's U.S. Pat. No. 6,581,594, incorporated by reference in its entirety.

Noise may also be reduced using soft-edge holes design as disclosed in ResMed's "Soft-edge vent" patents (U.S. Pat. Nos. 6,561,190 and 6,561,191) and commercially applied in the Mirage® nasal mask and Mirage® Full-face masks.

Other methods utilize diffuse materials such as filter like filter wool over the vent holes such as that used on Fisher & Paykel's Aclaim™ mask.

Vents may also come as separate components that are subsequently attached at the mask inlet air entry point (e.g. elbow). These vents are considered attached to the mask assembly, though technically situated adjacent to a mask frame.

Air 'slot' vents have also been developed to reduce noise by causing the layer of vented air to pass through a relatively thin slotted-hole in order to reduce noise. Variations of this design include slots circumscribing an axis to the inlet pipe (e.g. Respironics Whisper Swivel vent) or a novel variation by ResMed that passes the air over a relatively long thin slot (e.g., see U.S. Pat. No. 6,691,707, incorporated by reference in its entirety, and commercially embodied in the ResMed Ultra Mirage® Nasal Mask).

All current CPAP mask interfaces vent at, near or adjacent to the mask interface. This results in a common irritating noise source in close proximity to a user (say within the diameter of a human head) and within a bed-width distance of a bed partner.

Air "Jetting"

Existing vent holes are fairly simple in nature. They are basically holes 'drilled' into mask components. These holes generate a thin jet of air that flows in the direction of the axis of the hole. This direction is considered by engineers to minimize disturbance of the patient and also the bed partner. Blowing vented air directly onto a bed partner (when facing each other), will be irritating and potentially affect treatment of the patient as one bed occupant's disturbed sleeping and movement may result in disturbance to the other.

The vent holes may also be angled to reduce direct interference, however, there is still the possibility of vented air blowing onto the patient especially when it is deflected by bedding materials.

The vent holes may also be mounted to rotating elbows that are attached to the mask frame. These rotating elbows traditionally provide freedom of tubing direction for the patient, e.g., over-the-head or downwards. Angled vents mounted to rotating elbows allow the vented direction to be selectable in the direction of the air tubing that is attached to the elbow. Although this is regarded as one of the better vent directions, it may still jet onto a patient or bed partner and/or create noise if interfered by bedding materials.

Another method of reducing the 'jetting' effect is by creating a more diffuse vent flow pattern. This may be achieved by the use of very small holes or by creating a multiplicity of tortuous paths for the vented gas. These vents may be difficult to clean, have minimal life, and can block easily with grit or even condensation (water droplets).

Whilst conflicting requirements will generally lead to a suitable balance acceptable to engineers, many consumers have their own preferences or requirements. For example, a patient may be satisfied with the vent noise level, however may be irritated by the chosen vent direction of the air jets.

Masks from DeVilbiss have also shown an air vent with selectable jet direction that may be rotated (user selectable) to a desired angle relative to the mask frame and therefore patient. However, sleep is an active exercise and the body will naturally move during the night or treatment session. A patient for example may not jet vented air onto their bed partner until part way through the sleep session when the patient's body or head moves, causing subsequent irritation and loss of quality sleep.

Pressure Swings and Breathing Comfort

Pressure swings is known in the art as the actual pressure change experienced at or near the patient airways between inhalation and exhalation. For example, a patient breathing on a flow generator machine set on 10 cm water pressure through a mask interface will experience a higher pressure on exhalation (say 12 cm), and a pressure drop on inhalation (say 8 cm); the resultant pressure swing in this example is 4 cm. Generally, the lower the swing results in less work of breathing on a patient, and therefore increased breathing comfort.

Excessive pressure swings can lead to non-compliance of a patient. Several products are available to treat these patients. One such device is known as a bi-level flow generator. Examples are the Respironics BiPap™ and the ResMed VPAP™ and can be set to reduce pressure on exhalation, therefore reducing the work of breathing (i.e. work of exhalation). Respironics also markets a C-Flex™ system where the device has improved breathing comfort by reducing the work of breathing by controlling the blower characteristics electronically.

Although bi-level flow generators are designed to produce pressure swings to treat the patient, breathing effort on exhalation can be modified so that minimal exhalation effort is required (that is more comfortable) when these devices are used on patients with sleep apnea who have unsuccessfully used a constant pressure CPAP device, as CPAP devices do not significantly reduce the effort required to exhale.

Other methods to reduce swings may include valves and also flow generators designs that have carefully considered blower design characteristics.

System Compatibility and Performance

Most manufacturers of CPAP systems develop mask interfaces and flow generators as a system where the flow generators are engineered to function optimally with that manufacturer's mask interfaces. Many CPAP machines do not however function optimally or even poorly with another manufacturers' masks, resulting in loss of performance and even comfort can be compromised.

Accordingly, a need has developed in the art for a system that addresses one or more or all of the above challenges.

SUMMARY OF THE INVENTION

One aspect of the invention is directed to a CPAP-type device that offers a mask and flow generator system whereby the mask and the flow generator are specifically designed to function as one cohesive system, e.g., a closed system, in regard to vented or exhausted air.

Another aspect of the invention is to provide a ventless mask CPAP (VMCPAP) system (interface/air delivery system and flow generator) with improved functionality, performance, and/or increased comfort to the patient. That is, the VMCPAP system provides a quiet interface at the patient or interfacing region and also eliminates the irritation of air jetting onto oneself and/or bed partner.

Furthermore, it an aspect of the invention to provide novel options or embodiments not previously possible with current treatment systems, e.g., by actively venting instead of passively venting.

Another aspect of the invention relates to reducing the impedance and/or increasing the pressure differential over current methods between the region of exhaled/exhausted gas from a patient (externally adjacent to a patient's airways) to atmosphere (environment surrounding the patient) whilst venting the patient's exhausted gas to a remote vent location (relative to the mask interface) thus moving noise or irritating airflow source (e.g. jetting) a significant distance from the patient and/or bed partner's ears/head or otherwise to a suitable location where the noise and jetting source may be suitably attenuated.

In still another aspect, the invention relates to increasing the pressure differential at a vent between the inside of a mask and atmosphere to increase flow and therefore washout a greater proportion of $CO_2$ from the patient's exhaled breath. This can be achieved by increasing internal mask pressure (with the risk of over treating a patient with excessive pressure) or preferably negative pressure on the atmosphere side.

In yet another aspect, the invention relates to moving a noise source (vent) a further distance from the patient's ears to reduce noise and irritation thus improving comfort. A remote vent location may be a significant distance from the patient's head, a novel approach not previously achieved in current CPAP systems.

Another aspect of the invention relates to reducing flow impedance and/or providing a greater pressure differential through a remote vent at the end of long tube to encourage more effective $CO_2$ washout despite physical mask internal dead space being increased.

In another aspect of the invention, there is provided a CPAP system comprising a mask provided to a patient in use, the mask including a breathing chamber, a flow generator in communication with the mask, a positive pressure line to provide positive pressure air from the flow generator to the mask, and a vacuum line provided to positively extract exhausted gas from the breathing chamber.

Another aspect relates to a flow generator structured and/or controlled to assist in the remote exhaust of $CO_2$ gas from the system. Such a flow generator may include flow path to direct gas through a muffler and/or anti-bacterial filter, prior to exhaust. The flow generator may also or instead include a $CO_2$ monitor to measure the concentration of exhaled gas, which can be used as a parameter in a feed back control algorithm, whereby the flow generator adjusts the CPAP pressure to control the exhaled $CO_2$ to a healthy level. The flow generator may also include a valve coordinated with the patient's breathing cycle, e.g., closed during inhalation and open during exhalation, to reduce peak inhalation flow and consequently reduce power consumption of the fan (which is beneficial for a battery powered (portable) system) and/or reduce the cross-sectional size of the tubing (which results in less noise).

These and other aspects will be described in or apparent from the following description of preferred embodiments.

BRIEF DESCRIPTION OF THE DRAWINGS

FIGS. 12 and 13 illustrate a nozzle and elbow assembly according to an example of the present invention.

DETAILED DESCRIPTION OF ILLUSTRATED EMBODIMENTS

Preferred or exemplary embodiments of the invention will be described in reference to FIGS. 1-15. Initially, only a general description of the components for preferred embodiments will be described, and this will be followed with a further description of features, advantages and other options.

Aspects of the air delivery methods or systems described below may be incorporated into other systems such as those described in U.S. Patent Application No. 60/775,334, entitled Mask Pressure Regulation in CPAP Treatment and Assisted Respiration by Dynamic Control of Mask Vent Flow and filed Feb. 22, 2006 the entirety incorporated herein by reference.

Figure 1:
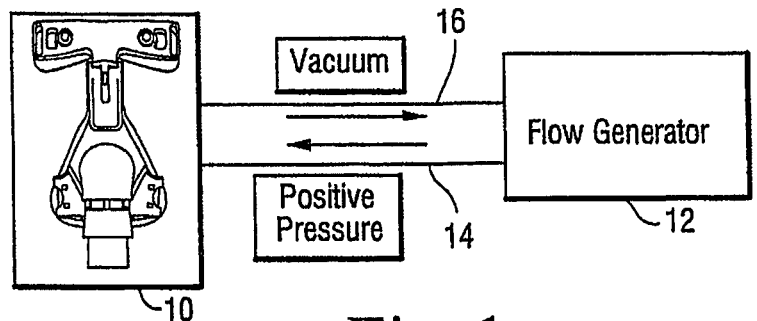
FIG. 1 schematically illustrates a system according to a first embodiment of the present invention.

FIG. 1 shows an assembly according to a first embodiment of the present invention. The assembly includes a mask 10 in the form of a full face mask, although nasal mask, nasal cannula, prongs, nozzles or puffs are also within the scope of the present invention. Mask 10 is in communication with the flow generator 12 via a positive pressure line 14 and a vacuum line 16. Positive pressure line 14 may take the form of an air delivery tube, as is known in the art. Vacuum line 16 is in communication with the interior of the mask, e.g., the mask breathing chamber, to actively or forcibly extract exhaled $CO_2$ from the interior of the mask and deliver it to a remote location, e.g., in this case the flow generator and subsequently to atmosphere. The flow generator 12 will include a source of positive pressure generation for positive pressure line 14, as well as a source of negative pressure generation, for vacuum line 16. In examples described below, the vacuum line 16 may also be referred to as a return line that need not be provided with a negative pressure generator or otherwise subject to vacuum pressure.

Figure 2:
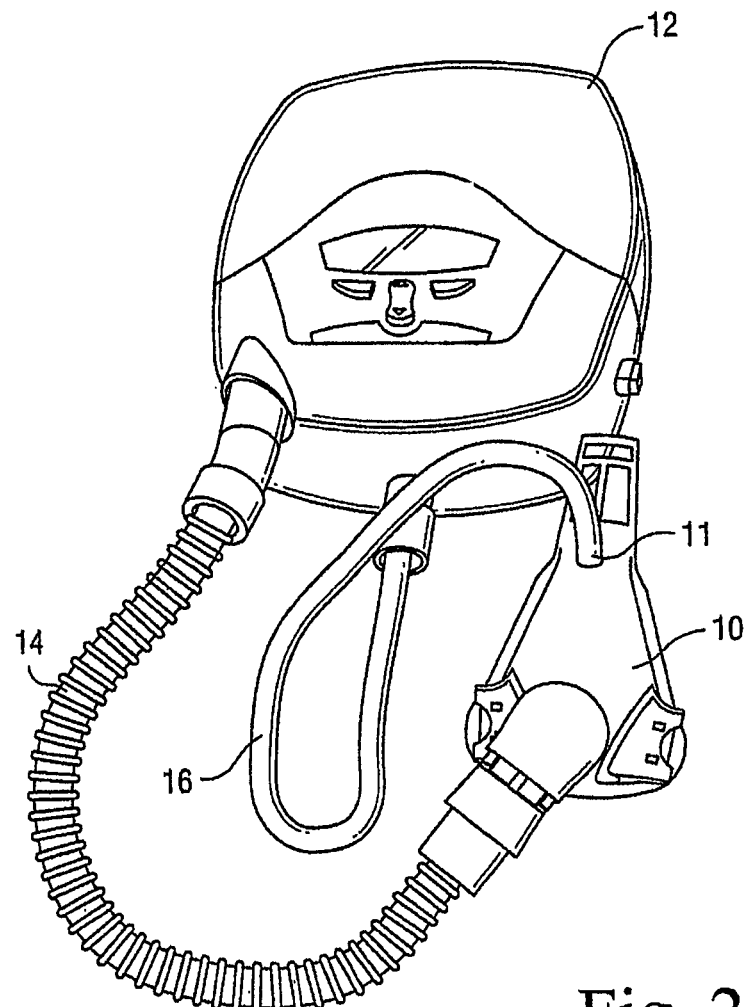
FIG. 2 illustrates a first prototype made according to the embodiment of FIG. 1.

FIG. 2 illustrates a first prototype made according to the schematic diagram of FIG. 1. Like reference numbers have been used to indicate like parts. The mask 10 includes an access port 11 conveniently provided on the front of the mask for connection with vacuum line 16.

Figure 3:
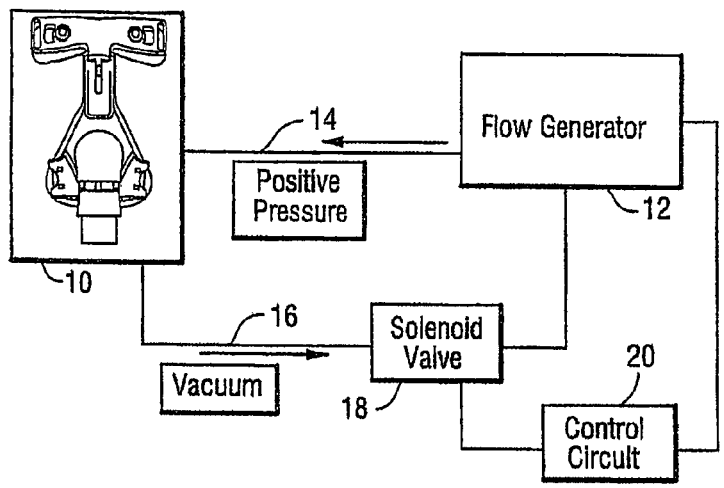
FIG. 3 schematically illustrates a system according to a second embodiment of the present invention.

A system according to a more advanced embodiment of the invention is schematically illustrated in relation to FIG. 3. The system includes a mask 10, a flow generator 12, a positive pressure line 14, and a vacuum line 16. In this respect, the embodiment of FIG. 3 is similar to the embodiment of FIG. 1. FIG. 3 also includes a solenoid valve 18 in communication with vacuum line 16. A control circuit 20 provides signals to operate the solenoid valve in dependence on pressure or flow signals, or detected $CO_2$ levels. For example, control circuit can operate solenoid valve based on the breathing cycle of the patient, which can be detected using flow and/or pressure sensors, as is known in the art.

Figure 4:
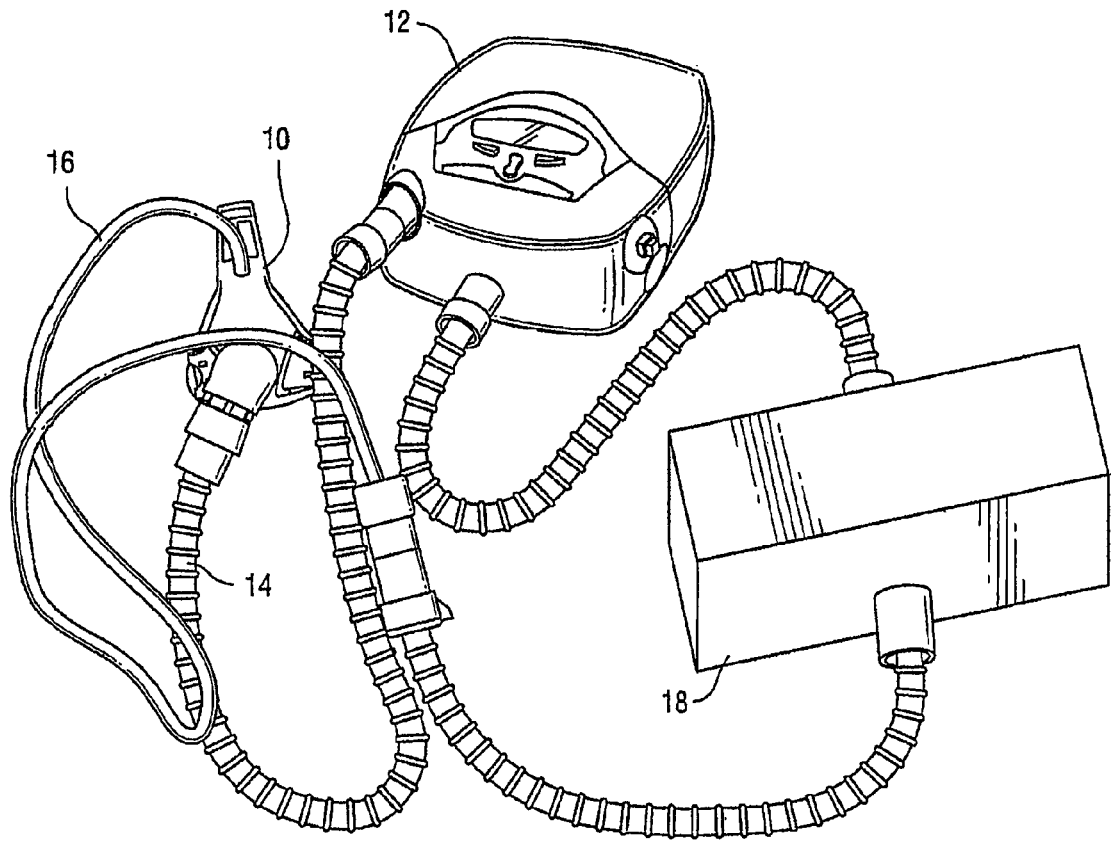
FIG. 4 illustrates a second prototype made according to the embodiment of FIG. 3.

FIG. 4 is a second prototype illustrating an embodiment of the invention made according to the schematic illustration shown in FIG. 3. Like reference numbers denote like parts. FIG. 4 includes a relay box 21 that may support valve 18 and at least a portion of control circuit 20. A portion of control circuit 20 may be included as part of the flow generator 12 as well.

Figure 4A:
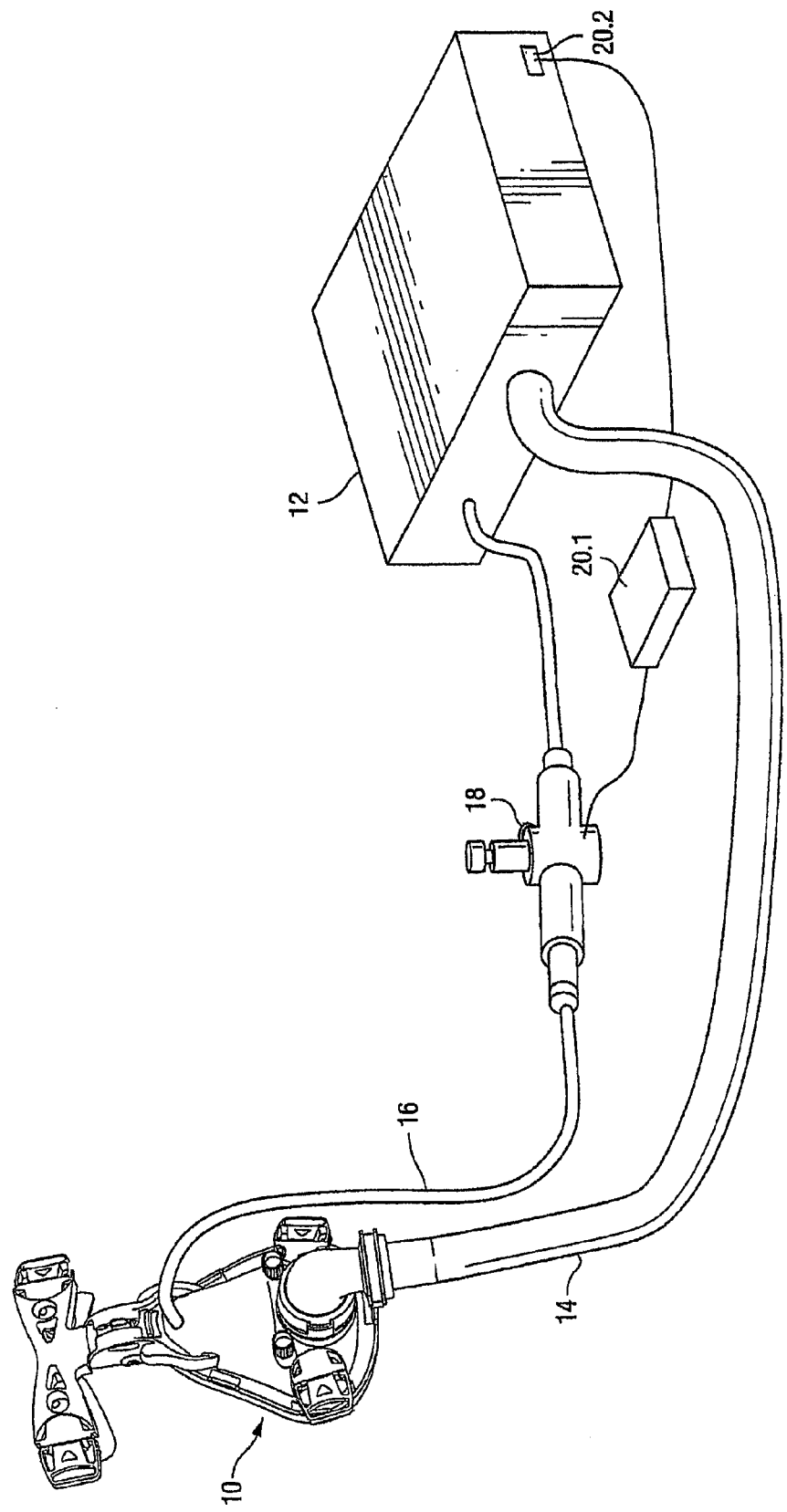
FIG. 4A illustrates a system according to another embodiment of the present invention.

FIG. 4A illustrates an embodiment of a system that has two flow sources that influence the pressure within the mask. One source is positive pressure line 14 that provides positive flow to the mask volume from atmosphere. The other source is vacuum line 16 that provides negative flow away from the mask volume to atmosphere and acts as the venting for the patient. Because of the partially enclosed volume of the system a pressure is developed within the system, that can be controlled from one or both of the two sources to meet the requirements of the patient. Increasing the flow from the positive source and/or reducing the flow from the negative source can increase pressure within the system.

A first mode of operation uses a continuous negative flow source and provides venting to the patient throughout the breathing cycle. The venting draws out exhaled air and moisture within the mask volume.

A second mode of operation utilizes solenoid valve 18 to control the negative flow source. Valve 18 is preferably in communication with a signal amplifier 20.1 that is in communication with the output (signal) of the flow generator 12. Valve 18 is synchronized to the breathing of the patient so that the negative flow source (line 16) would draw air from the mask volume only when pressure within the system needs to be lowered to allow the patient to exhale against a lower pressure than the pressure they were using for treatment. Negative flow source (line 16) would stop drawing air from the volume when the pressure within the system could be increased without discomfort to the patient's exhalation and the requirements of treatment.

A separate flow generator motor to that of the blower motor creates the negative airflow path; both motors have similar mechanical capabilities. In exemplary embodiments, the system uses a 6 mm bore tube as the negative airflow path and 22 mm bore tubing for the positive flow path. The length of each tubing is, e.g., 2 m.

In the second mode of operation, the flow generator 12 detects the expiration and inhalation of the patient though the positive path tube (line 14) and sends a signal through outputs to activate and deactivate solenoid valve 18 in relation to the signal received. In this example, a 2-way normally off (open states allow airflow) solenoid valve was used and the electrical signals were sent through the RS 232 communication port 20.2 from the flow generator. When the signal is switched on "high", solenoid valve 18 closes thereby stopping the negative flow path created by the vacuum blower. When the patient inhales solenoid 18 is closed stopping the venting from the system, when the patient approaches exhalation solenoid 18 is open to allow venting. In doing so the patient's comfort on exhalation is improved as the pressure that he/she exhales against within the mask system is at the optimal level to allow for appropriate treatment and allowing the most comfort to the patient.

A further embodiment includes a system without a negative flow source with an extended tube that extends to the point of venting a significant distance away from the mask system with the possibility of venting to atmosphere near the positive pressure source.

FIGS. 1-4A illustrate an embodiment of the present invention that operates on the premise of a closed system within the interface on the patient's face. It is because of this closed system that the patient has the benefit of perceived "soundless" CPAP treatment. In order to provide closed system treatment, ventilation is preferably provided to the patient without reducing the perceived soundless environment of the patient. This outlet for the ventilation should be placed in a position that should reduce or eliminate noise that may occur in open system CPAP treatment.

Figure 5:
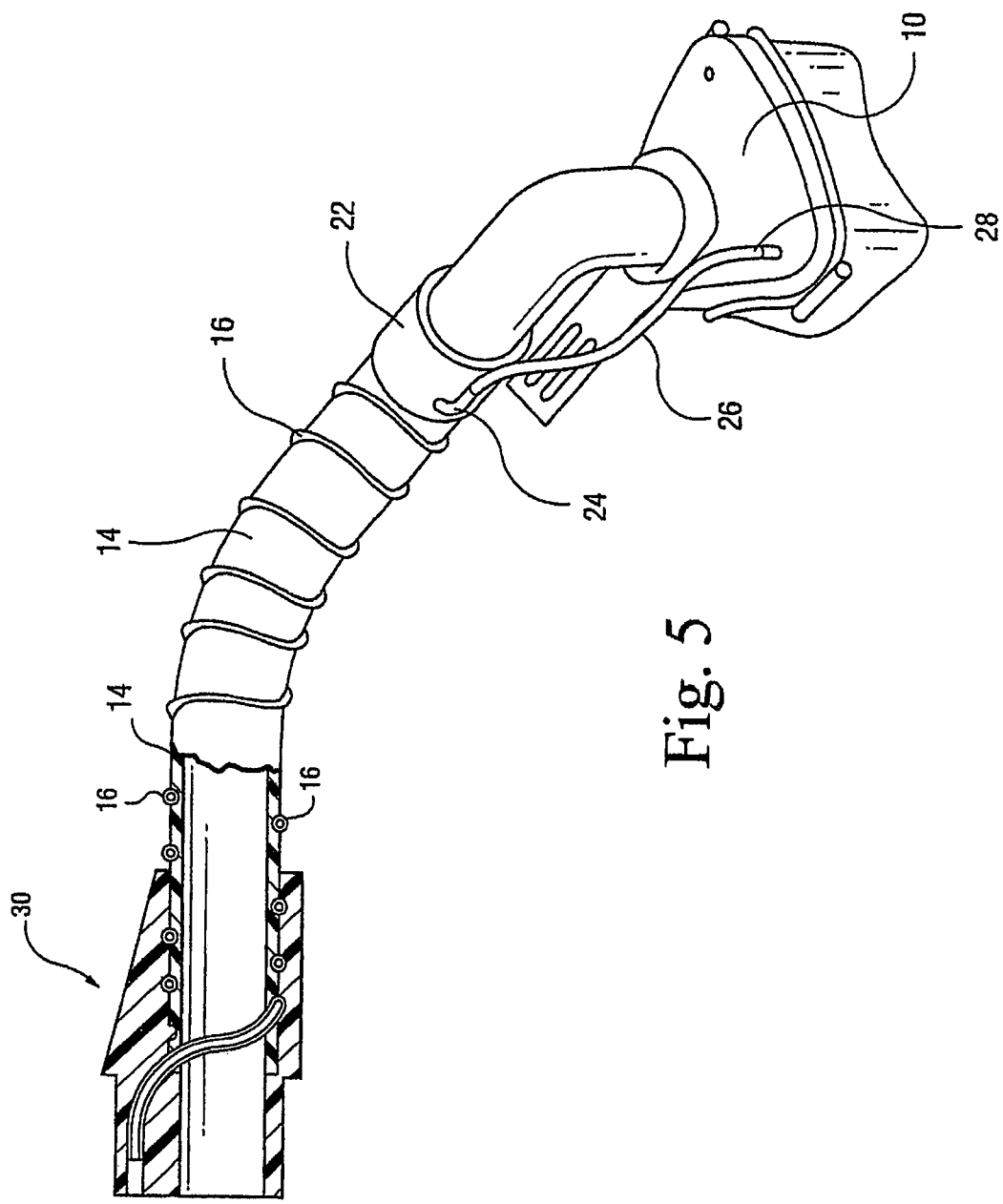
FIG. 5 illustrates a positive pressure line combined with a vacuum line.

Although the embodiments of FIGS. 1-4A illustrate positive pressure line 14 and vacuum line 16 which are independent or isolated from one another, the positive pressure and vacuum lines may be integrated into a single assembly as shown in FIG. 5, which is known from German Patent No. 199 54 724 A1, incorporated herein by reference in its entirety. In this embodiment, positive pressure line 14 takes the form of an air delivery tube which is spirally wound with vacuum line 16. Positive pressure line 14 includes a first end 22 adjacent mask 10 which includes an aperture 24 for accessing an exposed end 26 of vacuum line 16. Mask 10 includes a port 28 to receive exposed portion 26 of vacuum line 16. Positive pressure line 14 includes a connector 30 for attachment to a flow generator.

Figure 6:
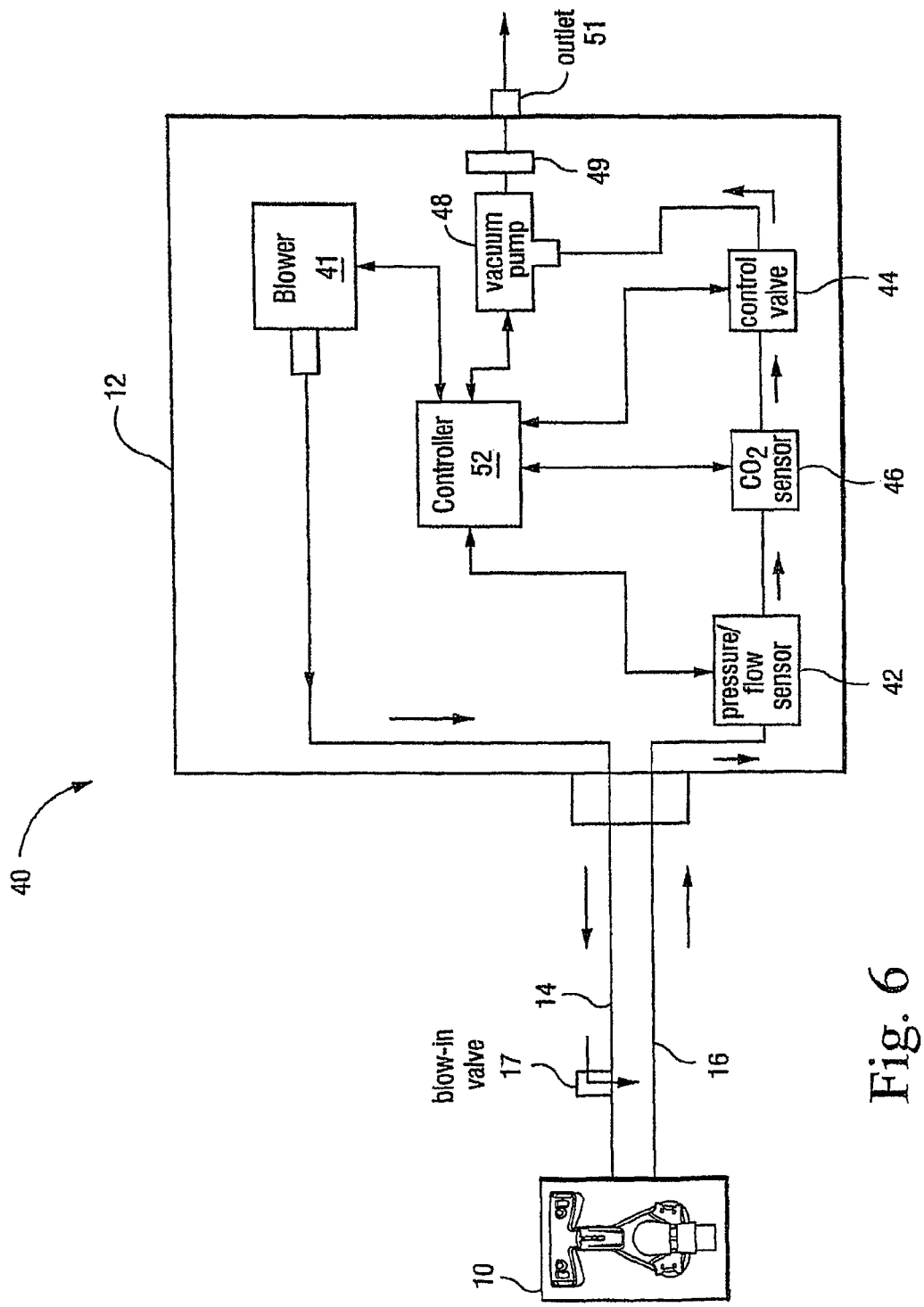
FIG. 6 schematically illustrates yet another system according to an embodiment of the present invention.

FIG. 6 schematically illustrates a system 40 according to yet another embodiment of the present invention. System 40 includes a mask 10 and a flow generator 12, as described in previous embodiments. Mask 10 is in communication with flow generator via positive pressure line 14 and vacuum line 16, which may be separate or integrated according to the embodiments described above. System 40 includes a blower 41 to supply pressurized gas to positive pressure line 14.

Exhaust gas which is conveyed by vacuum line 16 is directed to a pressure/flow sensor 42, a control valve 44 and a $CO_2$ sensor 46. A vacuum pump receives the exhausted gas from the $CO_2$ sensor 46 and delivers it to an outlet 51 to exhaust the gas to atmosphere.

The $CO_2$ sensor may measure the concentration of the exhaled gas, prior to muffling the gas. This allows effective $CO_2$ monitoring, e.g., via a suitable feedback control algorithm, whereby the flow generator adjusts is CPAP pressure to control the exhaled $CO_2$ to a certain healthy level.

The valve 44 is preferably positioned downstream of the $CO_2$ sensor 46, but upstream of the pump 48 and/or muffler 49. The valve 44 is preferably closed during inhalation, and dining exhalation it would be open. This would bring advantages to the flow generator design, because it would reduce the peak inhalation flow from 120 l/min to something less than 100 l/min, e.g., about 60 l/min. This in turn would significantly reduce the power consumption of the fan, and may be very suitable for a machine that needed to run on battery power. Also, it would be very suitable for smaller bore tubing, as at 60 l/min the hose loss is much less. Finally, it would be very advantageous for radiated flow generator noise because, for the same losses, smaller fan and muffler apertures can be used. An average diffuser flow is still required down the expiratory hose. Another advantage is that the positive pressure tube does not need to be 22 mm; instead it can be between 10-15 mm.

A further improvement could be to add a second flow meter, on the exhaled gas side, possibly between the $CO_2$ sensor 46 and the exhalation control valve 44. This might be useful in more completely monitoring the patient flow rates and controlling the system.

In general, other sensors in the flow generator that monitor the returned gasses on the vacuum or return line may be used in flow generator control. In one example, if the flow in the vacuum line to the flow generator is zero, the vacuum line pressure at the flow generator is equal to the mask pressure. This information (in the form of a signal) would be useful for mask pressure control, e.g., if the vacuum line valve is off during inspiration when the mask pressure would be expected to drop due to swings. The measured pressure on the vacuum line could then be used to boost the output to minimize the pressure drop. Other sensors in the system that are used to analyze gasses in the vacuum/return line could be used to control the flow generator. For example, a humidity sensor, an $O_2$ sensor, and/or a temperature sensor, etc., could be used to analyze the vacuum/return line gasses to provide a control parameter or feedback signal to the flow generator control algorithm.

A flow generator using the valve 44 (e.g., see FIG. 6) would ideally include a safety valve, e.g., a magnetically operated anti-asphyxia valve (not shown), to vent exhausted gas in the event of a power failure or improper operation of valve 44. This safety valve can take the form of a flexible flap provided along the air flow path, but it is preferably near the patient interface, e.g., a flexible flap in the mask wall. The safety can also be in the flow generator, e.g., in the form of hardware that customarily opens the valve if it is closed for more than a predetermined amount of time, e.g., 5 seconds. This safety feature can be implemented using hardware in the flow generator.

Additional Benefits with Humidifier

As mentioned above, the use of a flow generator having a controlled valve 44 (FIG. 6) has potential benefits. There are additional potential benefits when the flow generator is used with a humidifier. For example, the use of a valve as described above limits the flow to atmosphere within the breath cycle (low flow during exhalation), hence reducing the overall average flow of the system. This can be beneficial for the requirements of the motor (not needing to be so powerful). Another benefit is that less water is used by the humidifier. For example, if the flow rate is reduced from 120 l/min to 60 l/min, the water tank of the humidifier can change from 350 mL to 175 mL capacity, so for a given power output it will heat up more quickly, or for the same warm up time less power will be used.

It may also be possible to provide humidity only upon inhalation to reduce humidifier power requirements by a factor of 2.

Muffler/Anti-Bacterial Filter

A suitable noise-reducing device, e.g., a muffling system 49, may be provided between the vacuum pump 48 and outlet 51. An anti-bacterial filter may be provided before the exhaust exit, to reduce the possibility of cross contamination of others, e.g., other patients in a hospital or clinical environment, or the patient's bed partner. The components are in communication with a controller 52.

Figure 7:
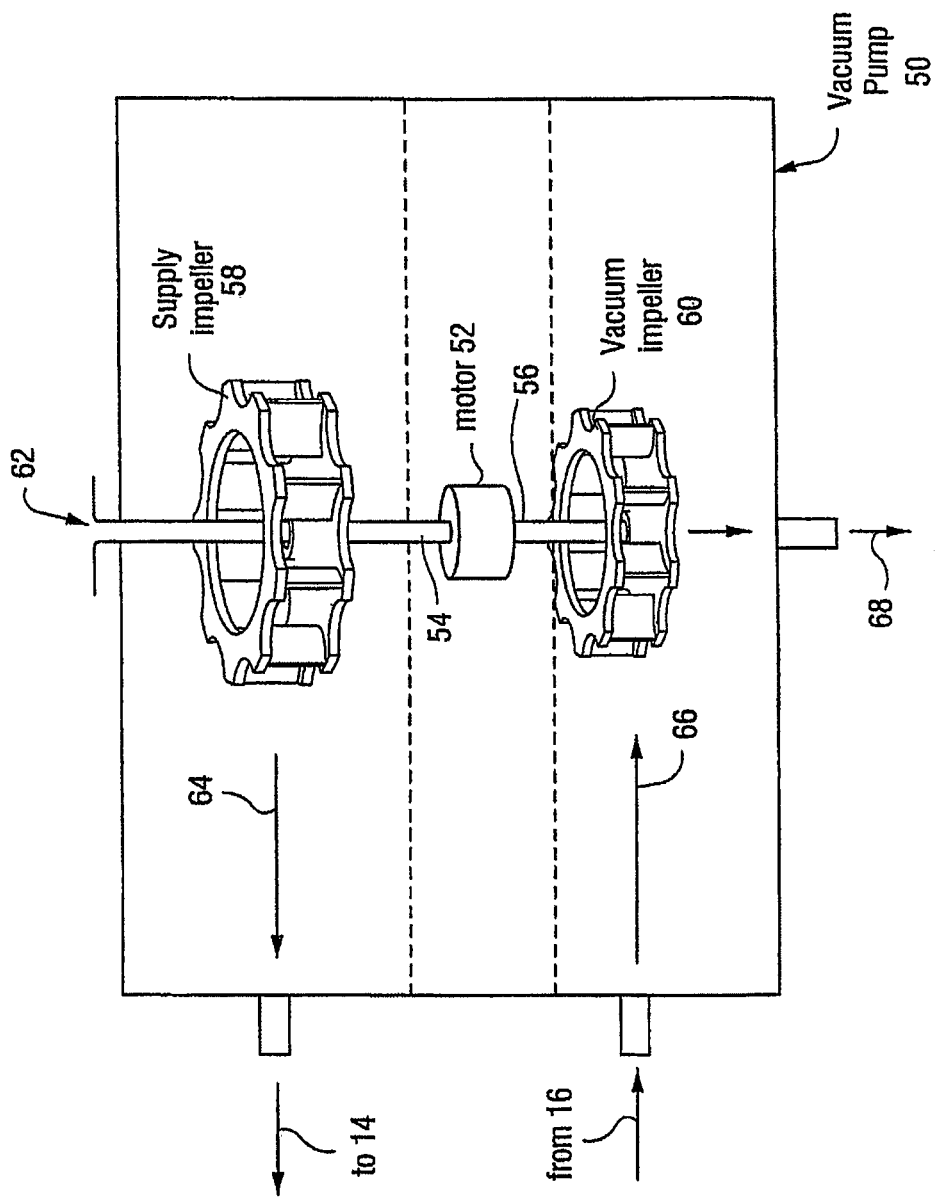
FIG. 7 illustrates in a schematic fashion a dual pump (positive and negative pressure) according to still another embodiment of the present invention.

While FIG. 6 shows that vacuum pump 48 and blower 41 are separately formed, they may take the form of a doubled-ended pump utilizing a single motor. As shown in FIG. 7, vacuum pump 50 includes a motor 52 including first and second shaft ends 54 and 56. First shaft end 54 is fixedly secured or otherwise provided to a supply impeller 58, while second shaft end 56 is fixedly secured or otherwise provided to a vacuum impeller 60. Supply impeller 58 receives intake air via an intake 62, and after pressurization the pressurized gas is directed along a path 64 to positive pressure line 14. Path 64 may be formed of one or more conduits and/or volutes. See, e.g., U.S. patent application Ser. No. 10/864,869, filed Jun. 10, 2004, incorporated herein by reference in its entirety. Vacuum impeller 60 receives exhaust gas from vacuum line 16 and exhaust the gas to an outlet port 68, which is typically open to atmosphere. Gas is directed from vacuum line 16 to vacuum impeller 60 along a path 66, which may include one or more conduits and/or volutes.

Gas in the vacuum pump 50 can be caused to flow in the intended direction varying the size of the impellers 58 and 60. In addition, each of the impellers 58 and 60 include blades that are oriented in such a fashion as to direct the gas in the proper flow direction.

Figure 8:
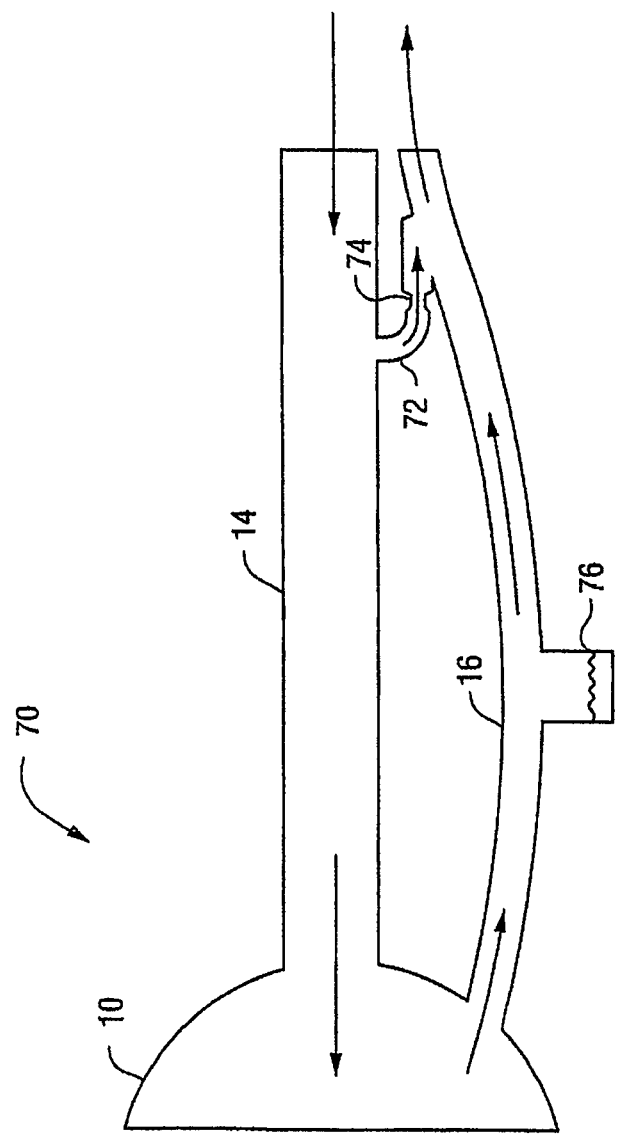
FIG. 8 illustrates a mask and conduit combination according to yet another embodiment of the present invention.

FIG. 8 illustrates a mask and conduit system 70 according to yet another embodiment of the present invention. System 70 includes a mask 10 as well as a positive pressure line 14 and a vacuum line 16. Directional arrows indicate the intended direction of gas flow in the system. To increase or enhance air flow in vacuum line 16, a bypass 72 may be provided to vacuum line 16. While a bypass is shown in the illustrated embodiment to communicate between the positive pressure line 14 and the vacuum line 16, the positive pressure line 14 may be substituted by an independent line which is provided with pressurized gas via a flow generator.

In any case, the bypass 72 preferably includes a venturi such that the velocity of air accelerates on the downstream side of the venturi. The venturi effect can be enhanced by providing a very narrow section 74. The high velocity of gas which is passing through the venturi 74 helps promote the passage of gas along vacuum line 16.

FIG. 8 also discloses a moisture trap 76 which is intended to collect any excess water contained within vacuum line 16. Trap 76 may include a cartridge which is disposed of when saturated, or the water can be re-routed to a humidifier for humidification of the gas provided to the patient.

VMCPAP Applied to Nozzle Assemblies

Figure 9:
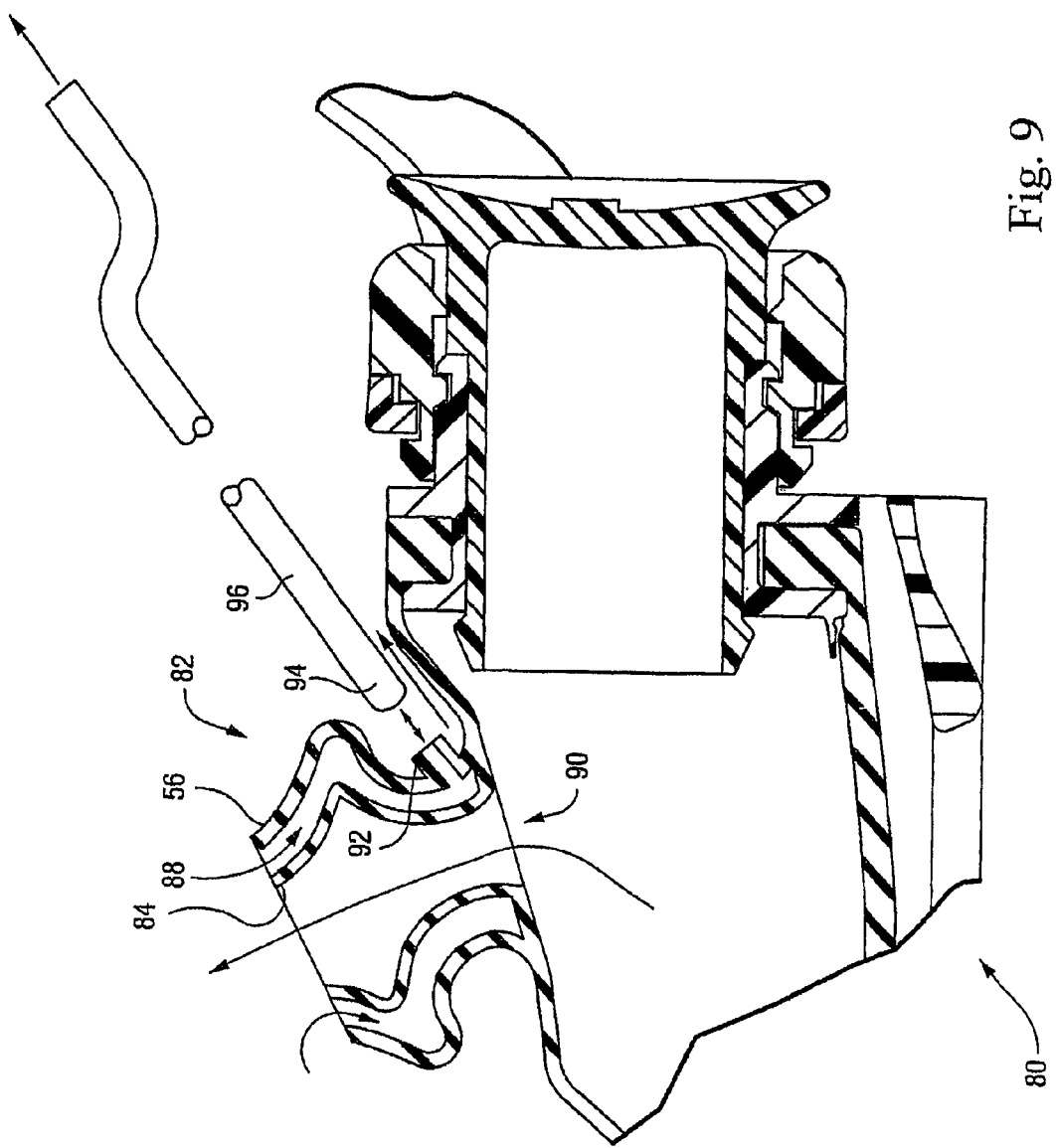
FIGS. 9 and 10 illustrate a mask assembly according to still another embodiment of the present invention.
Figure 10:
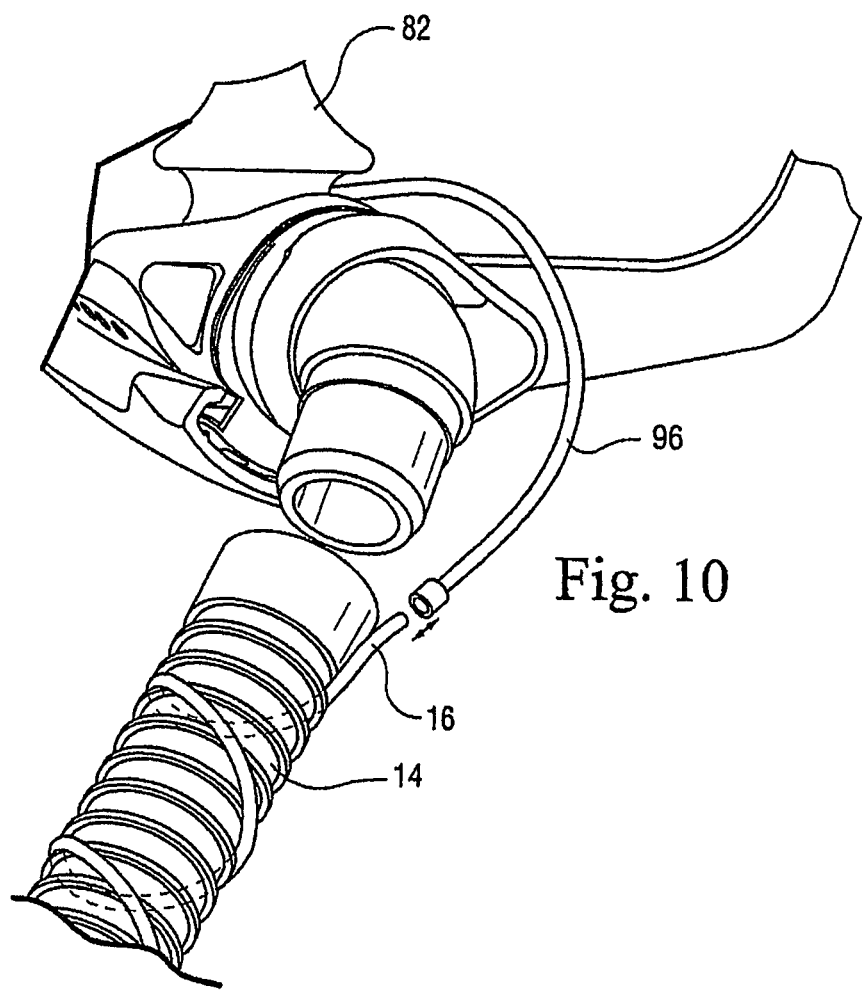

While the embodiments of FIGS. 1-8 all relate to the provision of a vacuum line to a nasal or an oro-nasal mask, embodiments of the invention also have application to other mask systems as well. For example, FIGS. 9 and 10 illustrate a mask assembly, the main components of which are described in ResMed's U.S. Provisional Application No. 60/632,193, filed Dec. 2, 2004, and International Application No. PCT/AU2005/000515, filed Apr. 5, 2005, each incorporated by reference in its entirety. Only a portion 80 of the mask system is illustrated. As shown in FIG. 9, the mask assembly includes a nozzle 82 which is structured to engage the nares of a patient. Only one nozzle 82 is shown in the drawing, it being understood that a second nozzle is provided for the patient's other nare. Nozzle 82 is provided with an inner membrane or wall 84 which defines with outer wall 86 a path 88 therebetween. Suitable spacers, ribs or other reinforcement elements may be provided to maintain the spacing between the walls 84, 86. A central aperture 90 allows pressurized gas to be delivered to the nares of the patient. Exhaled gas is guided along channel 88 and directed to port 92, which in this example is provided at the base of nozzle 82. The port 92 can be connected with an end 94 of a tube 96. As shown in FIG. 10, tube 96 can be connected to a vacuum line 16 which is helically wound about a positive pressure line 14 in the form of an air delivery tube. Of course, other arrangements are possible. For example, the channel 88 can be internally directed within the pressure chamber, instead of outside the pressure chamber as illustrated. Numerous other arrangements and modifications are within the spirit and scope of the invention.

Figure 11:
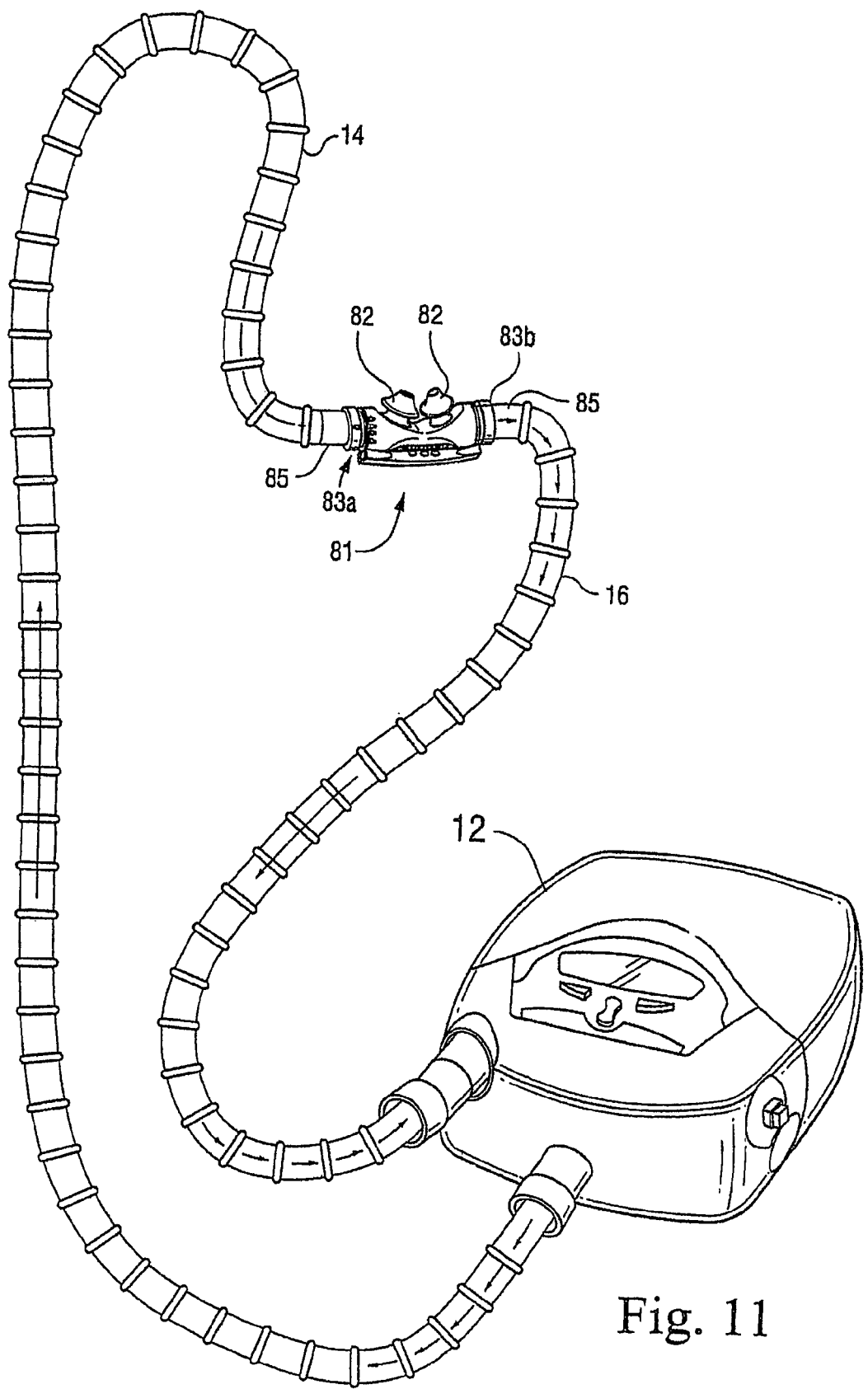
FIG. 11 illustrates a system according to an example of the present invention.

FIG. 11 illustrates another example of a mask system according to the present invention. The mask system includes a nozzle assembly 81 including two nozzles 82. Nozzle assembly 81 is structured to include two end portions 83a and 83b, each of which may be selectively provided with either a plug or an elbow 85, as described in ResMed's U.S. Provisional Application No. 60/632,193 and International Application No. PCT/AU2005/000515. In this variation, each end 83a and 83b of the nozzle assembly 81 is provided with an elbow 85, and an end plug is not utilized. One end portion 83a is in communication with a positive pressure line 14, while the other end portion 83b is in communication with a vacuum or return line 16. The positive pressure line 14 and the vacuum or return line 16 are coupled to or otherwise in communication with a flow generator 12, as described above. Flow through the system is in the direction of arrows.

FIGS. 12 and 13 illustrate yet another example of a mask system according to the present invention. Nozzle assembly 81 includes a pair of nozzles 82, as described above. In this example, elbow 85 includes a positive pressure line 14 while vacuum or return line 16 is helically wrapped about the positive pressure line. Elbow can be a standard ResMed "SWIFT"® type elbow, with the vacuum or return line wound about the elbow, or the vacuum line can be mounted integrally with the elbow 85.

Nasal assembly 81 includes a main body including at least one baffle 87 that directs gas from positive pressure line 14 just under the nozzles 82, where pressurized gas can be inhaled or provided to the patient or wearer. Upon expiration, exhaled gas is pushed or drawn through the nozzles such that the exhaled gas proceeds along the baffle 87 and towards the vacuum line 16, whereupon the exhaled gas is vented at a remote location.

FIG. 12 shows the nozzle assembly 81 with the elbow 85 in phantom to show how baffle 87 generally divides the main body into first and second chambers. Directional arrows generally illustrate the flow of gas through the system.

Figure 14:
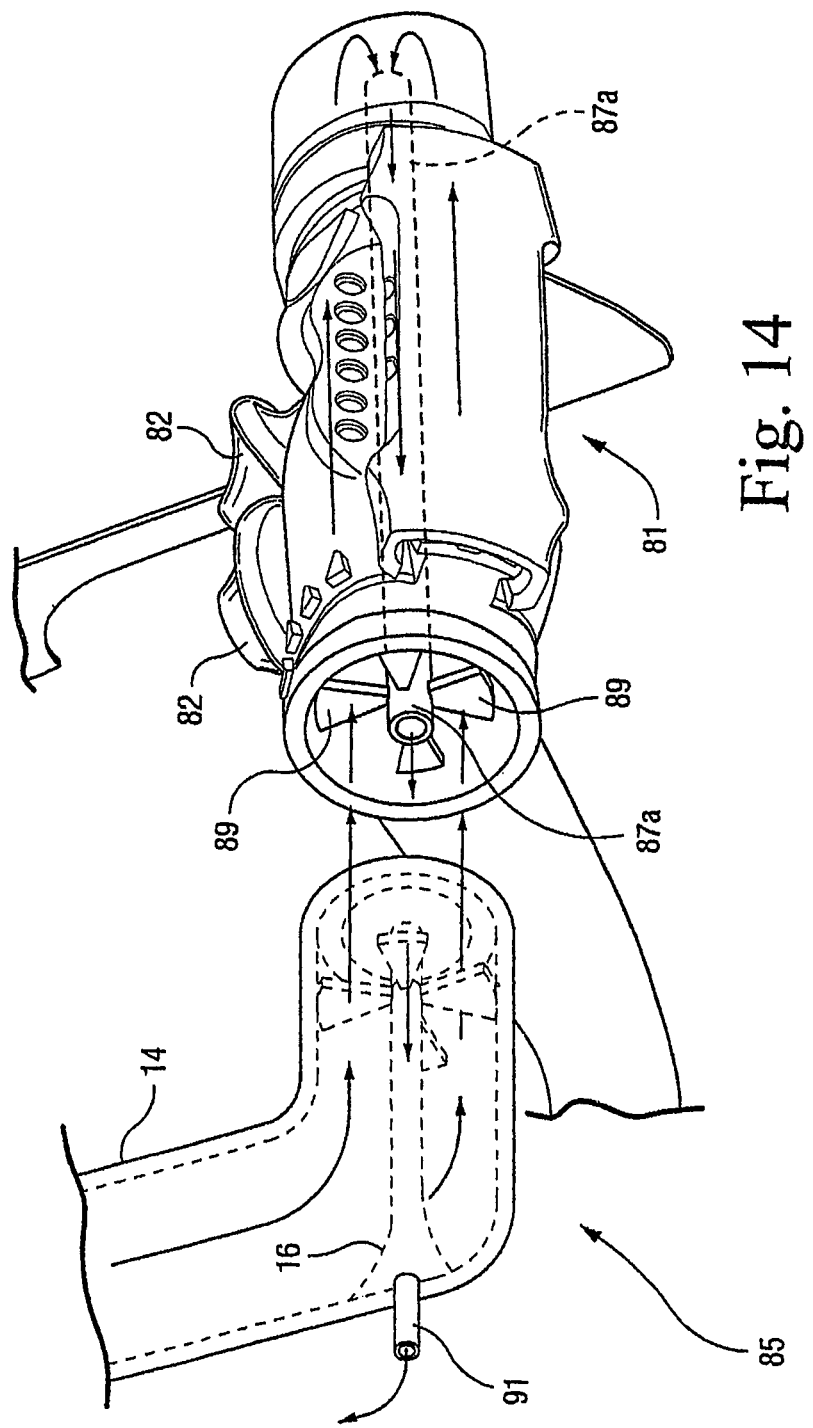
FIG. 14 illustrates a nozzle and elbow assembly according to an example of the present invention.

FIG. 14 illustrates a variation of one example of a nozzle assembly 81 including a centrally located baffle 87a in the form of a hollow cylinder 87a supported via one or support arms 89. Baffle 87a directs gas from the breathing chamber to the vacuum line 16, which in this example is formed within the elbow 85 in the shape of a hollow cylinder having a first end that communicates with the exposed end of baffle 87a and a second end that delivers the gas to a fitting 91 which can be connected to a small diameter tube, e.g., like that shown in FIGS. 5 and 12. This configuration allows for rotation of elbow 85 relative to the nozzle assembly without changing the orientation of baffle 87a. Moreover, baffle 87a may be formed as one integral piece with the elbow 85, as an extension of the vacuum line 16. Baffle 87a may be perforated along at least a portion of the length thereof to allow a suction and vacuuming action along the length of the baffle 87a, if desired.

Figure 15:
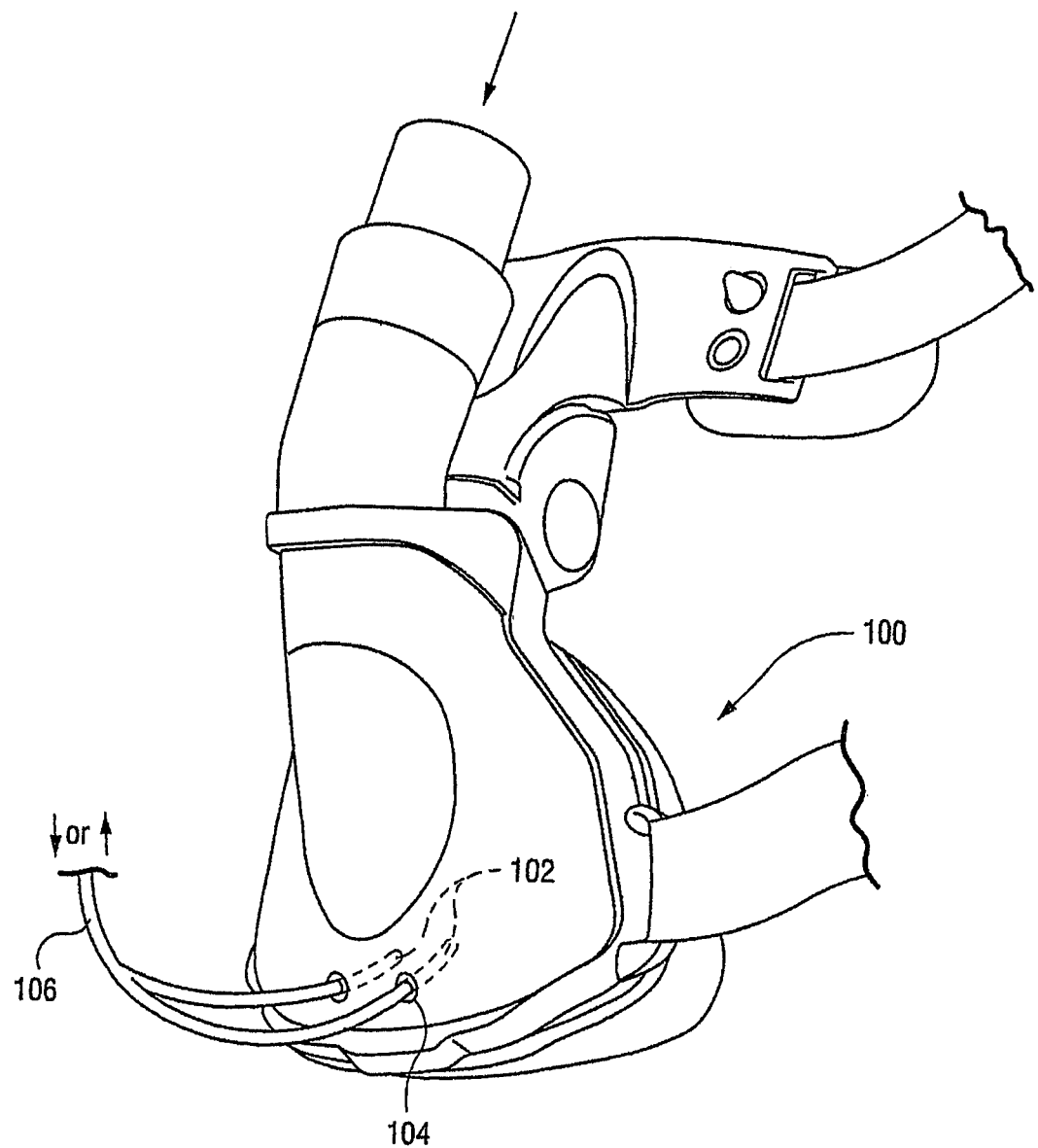
FIG. 15 illustrates a mask assembly according to yet another embodiment of the present invention.

In yet another embodiment shown in FIG. 15, the mask may include a nasal or oro-nasal mask 100, with the additional provision of nozzles 102. In this embodiment, the nasal or oro-nasal mask 100 is provided with positive pressure, and the nozzles 102 can be provided within or as part of the mask to act as a vacuum line. The nozzles 102 may also act to supply a supplemental gas directly to the patient, as indicated by the bi-directional arrows. Each nozzle 102 may be provided to one or more ports 104 located on the mask 100. Ports 104 may include appropriate structure to selectively and detachably receive a tube or conduit 106. Nozzles 102 may have a generally cylindrical shape (as shown in FIG. 15), or they may have a generally frustro-conical shape, similar to the shape of nozzles in FIG. 9.

Venting without Suction

The above embodiments have been described in relation to venting of exhaled gas where suction is applied to the vacuum line. However, such suction may not be necessary if the return line is dimensioned to provide the same pressure loss as a conventional mask vent, especially in conjunction with a flow generator including a valve 46 as described in relation to FIG. 6. Stated differently, the CPAP pressure could effectively flush the $CO_2$ by properly sizing the return line and proper operation of the valve.

Coaxial Tubing

The above described embodiments are described in relation to positive pressure lines with a vacuum or return line that is separate from or helically wound about the positive pressure lines. However, the tubing may include coaxial tubes as described in U.S. Pat. No. 6,345,619, incorporated by reference in its entirety. Having described components of the above embodiments, a further description of the operation and/or advantages is provided hereafter.

DESCRIPTION OF FEATURES, ADVANTAGES AND OTHER OPTIONS

Carbon Dioxide Washout by Negative Pressure Generation

Increased pressure differential by use of a negative pressure generator (e.g. vacuum pump) preferably built into a flow generator device. This may be built-in, attachable, or otherwise a stand-alone remote accessory that may be retrofitted aftermarket.

The negative pressure generator may be in many forms. For example, per FIG. 6, it may be a separate vacuum pump to the main positive pressure generator (blower) used to treat (ventilate) the patient. The pump could be diaphragm, motor driven impeller, or a piston.

The blower may also be double-ended utilizing a single motor (FIG. 7), e.g., as described in ResMed's U.S. patent application Ser. No. 10/360,757, filed Dec. 10, 2001, and Ser. No. 10/864,869, filed Jun. 10, 2004; each incorporated by reference in its entirety. For example, one end of the motor is attached to a blower housing used to deliver CPAP pressure to the patient's airways, whilst the other end of the motor drives a separate pump where the inlet is used as a vacuum source to draw the exhaled $CO_2$ from the mask interface. In this example, the vacuum pump is exhausted to atmosphere after suitable noise attenuation such as a muffler. The vacuum pump's impeller design may be different from the blower impeller to optimize the desired flow curve.

The vacuum may be monitored by a pressure sensor and/or flow sensor to ensure that the appropriate amount of negative pressure is generated to provide desired level of $CO_2$ washout.

The negative pressure generation may be continuous, however this would provide a greater 'leak' during inhalation where the patient requires the prescribed CPAP pressure. This may result in the flow generator's main blower to work much harder to ensure the correct treatment pressure is delivered. It is therefore preferable for the system (invention) to reduce or stop the negative pressure or 'leak' during the inhalation phase of breathing. This synchronized switching will be described further below.

An additional safety "blow-in" valve may be provided where the patient breathing airline is occluded and the vacuum line remains running or somehow develops a fault and wants to exceed safe negative pressure exposed to the patient's airways. The blow-in valve may in a simple form be a spring loaded inward folding flap valve that has a spring constant equal to the maximum negative pressure desired to prevent injury or discomfort to a patient in a failure mode.

Synchronized to Patient Requirements

The negative pressure generation may be synchronized to a breathing patient to maximize system performance. For example, the vacuum source may be engaged via a pneumatic solenoid switch where the vacuum pump running constantly or the vacuum source may be turned on/off (where the vacuum source is a separate unit to the main ventilation blower).

The VMCPAP system may also vary the profile of the exhausted air through the vacuum system and vent according to the patient's requirements. For example, the system may increase and decrease infinitely variably, in a plurality of steps, or at least two settings where $CO_2$ washout can be varied according to patient requirements. For example, a patient with a high proportion of expired $CO_2$, the device may produce an increased constant flow of $CO_2$ washout whereas a patient breathing in a slow and relaxed state may produce a slow regular cycle of $CO_2$ washout in synchrony with a breathing patient in a sinusoidal fashion. As described later, the device may balance this automated setting against other aspects of the patient, such as pressure swings.

The system may activate at a particular point of the breathing cycle to ensure the appropriate point to start the vacuum has the desired effect of $CO_2$ washout. There may be delays between triggering the device and actual flow of exhausted gas through the vacuum line and remote vent. For example, at higher pressures and faster breathing cycles, the device may switch the valve to negative pressure when the patient is near the end of inhalation rather than waiting till exhalation begins.

The device through electronic or other control may automatically adjust the triggering point according to patient need.

Some patients that re-breathe excessive $CO_2$ rebreathing may notice their breathing effort undesirably increased. This is a physiological effect. It has been known in some current art (for masks) that excessive $CO_2$ rebreathing is possible even though the vents are washing out $CO_2$. This is possible for a variety of patients that exhale relatively large amounts of $CO_2$ and is resolved by creating additional leak to allow increased washout such as removing a ports cap for example. (The port is usually blocked by the cap and can be used to engage with a pressure manometer or oxygen tubing in certain applications.)

If a patient observes their breathing comfort is less than optimal, another embodiment allows the patient to select the level of comfort desired. This may change the phasing of the vacuum line relative to the breathing patient as described above or otherwise increase the negative pressure generator's flow of air. This simple selection process by the user through an interface may also automatically modify other parameters in the system that affects comfort such as pressure swings (difference between maximum and minimum pressures experienced within a mask or patient's airways during breathing; higher pressure swings can be less comfortable for sleep apnea patients, for example).

The negative pressure source may be switched on and off, varied between high and low, or varied between high and off. If this principle is applied to a vacuum pump, it may either control the flow of gas electrically, mechanically, and/or pneumatically.

The variation could be achieved by changing impedance, variation of impeller physically (e.g. blade size and/or angle), changing the speed of the driving motor, variable gearboxes, constantly variable-ratio drive trains.

The pneumatic vacuum line may also be controlled by an electrically controlled solenoid where the vacuum pump is running at its maximum speed and an opening/closing valve controls the level of $CO_2$ washout. This valve may be infinitely variably opened or in multiple steps or simply opened and closed. In this example the valve simply stalls the flow of gas, however a diverter valve may also be used to open the valve, to atmosphere to allow air to flow to the vacuum pump; this may be useful to cool an electric driving motor.

In the last example, while the vacuum pump is not drawing $CO_2$ from the patient's exhaled air, the positive pressure side may be diverted back to the main blower or patient inhalation circuit to assist with delivering the positive pressure gas to the patient's airways.

Remote Gas Exhaust

By providing a remote source for vented gas to atmosphere, there is an elimination of vent airflow and jetting in a sensitive region to the patient and bed partner. Any annoyance from side effect of the device usage will lead to discomfort and potentially non-compliance of the medical equipment.

The remote location of the vented gas may be located part way along the air delivery tubing, or preferably run back to the flow generator device provided as a single unit.

The vacuum system may also be located totally separate from the flow generator. For example, the flow generator may be located on the bedside table, whilst the negative pressure unit (e.g. vacuum pump) may be located underneath the bed or under a pillow.

The vacuum pump may also be located as part of the mask or interface system (e.g. mounted to the mask frame or headgear) with a remote tubing opening located away from the patient. This embodiment assumes that a pump located close to the patient's ears is reasonably quiet to prevent discomfort due to noise.

Elimination of Air Jetting onto Patient and or Bed Partner(s)

Current mask systems have relatively fixed direction venting attached to the mask frames. As patients move their heads relative to their body, the vented air direction can change during the Course of treatment (during the night). As the patient faces their bed partner, some air can be directed towards them, which can disturb their sleep. Even if the venting direction is angled away from bed partner or patient's body, the bedding material may inadvertently redirect air onto them during the night.

Current art has also attempted to diffuse the airflow into many small jets or use of porous vents such as the Weinmann mask. These still however provide challenges to engineers to minimize noise and $CO_2$ rebreathing, blocking under humidity and cleaning issues.

By elimination of venting near the patient's head region, the common problem of jetting is improved over all current CPAP systems.

Elimination of User-Perceptible Noise

As the mask covers the patients airways it typically muffles the patient's own breathing and therefore reduces the noise of a breathing patient without wearing any mask system. The addition of the current art's air vent increases noise well above the volume of a breathing patient. As the invention has no vent at the mask, the invention provides a system that is actually quieter than a patient without any attached device in the vicinity of the patient and bed partner's ears.

The remote location is preferably back through the flow generator as the device typically is an enclosure with sound proofing materials to limit motor and blower noise. The flow generator is also typically located further away from the patient and bed partner's ears.

Although the noise source could be muffled (reduced) at the mask interface by special venting (e.g. mufflers, ResMed's fine mesh vent disclosed in U.S. Pat. No. 6,581, 594), this represents a much greater design challenge such as size, ease of cleaning and weight, therefore is not seen as a practical approach. To reduce the noise at the flow generator or other remote source provides many more flexible approaches to attenuate noise. Most flow generators are already enclosed with sourndproofing materials that provides a ready location to incorporate a vacuum pump. The exhausted $CO_2$ or other unwanted gas is simply discharged to atmosphere.

Pressure Swings Reduction

The device can also reduce Pressure Swings (difference between minimum and maximum pressure experienced by the patients airways or inside the mask interface during breathing on a flow generator) by engaging the vacuum pump at the appropriate point to reduce the peak pressure on exhalation that current art usually results in discomfort as the patient breathes out against increased positive pressure. Patients that cannot tolerate this pressure on exhalation may be prescribed with a bi-level device, which can reduce the pressure on exhalation. An embodiment of the invention essentially vents off excessive pressure during this phase to allow easier exhalation and therefore improve patient breathing comfort (whilst also reducing $CO_2$ rebreathing). Increased vacuum pump flow simply provides an additional leak (preferably on exhalation) that in turn reduces experienced pressure on exhalation, therefore providing improved patient comfort. This may be regulated by electronics while monitoring the patient's breathing cycle or simply by monitoring mask pressure.

An ideal pressure swing is at or near zero pressure differential. Embodiments of the invention can be developed in such as way to provide high rate of flow on exhalation to remove the majority of the peak pressure swing that would result to almost optimal breathing comfort unachievable with current designs.

Embodiments of the invention also provide an ability to close off venting during inhalation to allow the inspiratory pressure to be easier achieved, as there are fewer leaks to compensate for by the blower to reach prescribed pressure. A corresponding increase in vent flow is needed during the expiration phase to achieve the same average vent flow.

The patient may also be provided in a further embodiment a means to adjust the level of pressure swing depending on comfort desired or else a clinician/physician requirement. This may be a user interface or control panel. The machine may then optimize the vacuum pump to reduce $CO_2$ at the set rate of pressure swing. The patient can now select a preferred level of comfort without undesirable $CO_2$ rebreathing as embodiments of the invention simply compensate by increasing the level of $CO_2$ washout, e.g., by increasing flow through vacuum pump.

A further option of being able to control swings in the above-mentioned fashion allows certain patients (those with say lung-function illness as opposed to Obstructive Sleep Apnea) that require greater swings to be treated. These patients would regard the pressure swings as an advantageous feature. Therefore, embodiments of the invention may also utilize pressure swings (manually or automatically) between EPAP (minimum 0 cm of water pressure) and IPAP (up to 30 cm of water pressure) as required for the type of treatment mode. Pressure swings are fundamental to Bi-level flow generators. This may also be a patient or clinician selectable option.

The pressure swings reduction feature is preferably synchronized with a breathing patient and may be detected by way of flow sensors and/or pressure sensors in the device. Many computer controlled positive pressure devices already have the ability to sense part or all of a patient's breathing cycle, see, e.g., ResMed's VPAP™, which means that an electrical signal can be utilized to trigger the pressure swings control at the correct point during the breathing cycle.

Therefore the ability to control $CO_2$ is independent of all the previous compromising design requirements in mask and flow generator design. This is a significant aspect of the invention.

Condensation Elimination

In CPAP systems, humidification devices have been used (for example ResMed's HumidAire™) to introduce an increased level of humidity to the breathing air to improve therapy or comfort to the patient. Humidifiers do however have some drawbacks. For example, if the surrounding air is not warm enough to hold the moisture, condensation occurs in the breathing circuit (e.g. tubing or inside the mask interface).

It is desirable to increase humidification levels in the mask for the patient breathing air normally and not have excessive humidity as condensation or rainout. The problem is worse in cooler environments where air cannot hold as much moisture.

There are a number of devices (e.g. Fisher & Paykel) that may heat the air in the tubing so that greater humidity can be achieved without condensation, also known in the art as rainout. There are also other devices that may electronically monitor humidity levels and adjust the temperature control of the heating means that vaporizes or evaporates the water in a reservoir. Another aspect of the invention provides a simple method of condensation control without any complex controls in the humidifier or flow generator. Excess condensation is removed, e.g., by simple removal of fluid from where it sends to build up especially in the mask, but may also be in the tubing or air delivery line.

This condensation removing aspect may also be designed as a stand-alone device. The device may simply trigger when excessive moisture has been detected (e.g., fluid level sensors) to trigger a small pump or solenoid to apply vacuum to remove the condensation. This water may be collected for reuse by a humidifier or collected for later disposal.

One would now realize that excessive humidification that leads to condensation (or any effect leading to rainout) is not necessarily a complete negative side effect of current art humidifiers, but more correctly it is the condensation that accumulates in a mask or air delivery conduit that is undesirable. As described above a device is provided to remove excessive condensation no matter how much or how quick condensation is generated. Existing art that describes humidification control using temperature and/or humidity sensors and electronics is not required in this example.

Another aspect of the invention copes with any level of humidification and can control the level of humidified gas that enters a patient's airways. The system can therefore increase the level of leak to washout more humidified gas therefore reducing the level of humidity if so desired. This may also be electronically balanced with the patients other parameters such as $CO_2$ as described earlier.

Another aspect of the invention can provide a re-circulating circuit where excess water or rainout is trapped and either recycled for reuse by the humidification device (storage reservoir where the original humidification took place) and/or sent to a waste reservoir for disposal at the end of therapy.

Another embodiment of this invention allows the excess rainout or humidity to be dissipated to atmosphere. For example, electronic control and humidification sensor/s and/or temperature sensors in the vacuum line (according to the invention) may monitor when excessive condensation is about to occur therefore preempting rainout and may increase vent flow through the vacuum line accordingly.

The moisture in the vacuum line can be dissipated by heat and/or a porous device used to trap the moisture without spilling and may be subsequently dried or evaporated by the vacuum line air passing it before being discharged to atmosphere.

Higher Pressure Differential in Air Delivery Circuit

A higher-pressure differential as described earlier tends to improve the flow of gas from within a mask interface to atmosphere through a vent to reduce $CO_2$ rebreathing. The method could be described in Physics as the Bernoulli Effect where an increase in velocity results in a decrease in the static pressure.

A much simpler embodiment of the invention shall now be described. This includes a method to provide improved (increased) pressure differential across the vent by reducing air pressure below the surrounding ambient air pressure in the region (or near) where air is vented to atmosphere at a remote location.

This embodiment compares to the previous embodiment in that in its preferred form is integrated into the "air delivery system" and unlike previous embodiments, is not integrated into a flow generator device, does not require electronic control, nor does it exclusively require integration into a separate device. The so-called "air delivery system" includes the tubing, mask etc. that is situated between the flow generator device and the patient, but not including the flow generator.

This embodiment carries over many features of the other embodiments to increase flow out of a remotely located vent. As a reminder, simple remote vents may increase dead space and may increase $CO_2$ rebreathing. By encouraging air to flow from this significantly remotely located vent (say 2 meters away from the patient's mask), excessive $CO_2$ rebreathing can be avoided and benefits as stated earlier for example, remote noise source to increase patient comfort, are achieved.

One method to increase flow through the remote vent is by increasing the pressure differential across the vent, in this example, it is at the end of a two-meter exhaust or vent tube of say 2 to 15 mm internal diameter that is attached alongside the main air delivery tube (say 2 meter length and 22 mm internal diameter that supplies a positive pressure gas from a flow generator to the mask). The 22 mm tubing is attached to the inlet port of a mask interface attached to the patient, whilst the exhaust tube is routed from the mask with the open end either located inside the mask interface, attached to the surface with a through-hole into the mask interface, or otherwise attached to a mating component to the mask system such as a rotating elbow or swivel that is communicating with the patient's expired breathing gas (e.g. $CO_2$).

The other end of the exhaust tube is attached to a venturi assembly that is preferably inline with or otherwise connected to the main air delivery tube. This venturi assembly utilizes a bypassed flow of gas through another defined flow path preferably from a flow generator blower and is routed to atmosphere. This bypassed flow of gas is routed to a venturi pipe much like an automotive carburetor in function. The flow of air past an open ended tube (the other end of the exhaust tube) at a velocity that creates negative pressure zone at the opening of the exhaust tube increases the pressure differential between the air inside the exhaust tube and atmosphere. In effect, this assists with drawing expired gas (namely $CO_2$) from the breathing patient through the mask interface.

Further embodiments of this idea may include various locations for either or both the venturi assembly and also the vent/open-end to atmosphere. For example, the exhaust tube may also be longer or shorter compared to main air delivery tube and does not need to be tethered or integrated to the main tubing, however preferred. The vent may simply be located at a reasonable distance from the venturi assembly (e.g. 0.5 meters) and also a reasonable distance from the patient's or bed partner's ears to minimize noise disturbance, (e.g. 1.5 meters). Should the venturi assembly be mounted closer to the mask (and patient's head), it may be preferable to locate the exhaust tube (vent) remotely (e.g. 0.5 meters under the patient's pillow and behind the bed), while the main delivery tubing is routed towards the side of the patient. This last example demonstrates the flexibility of this embodiment of the invention whether it is configured as an integral assembly or gas paths independently provided for patient freedom or preference.

The outlet to atmosphere from the venturi device may exit directly to atmosphere or be routed through a muffler to reduce noise, or may be routed to one or more gas sensors to analyze gases to make necessary adjustments to the device or system.

The venturi device may also be adjustable for example, if the diameter of the venturi is reduced to increase the velocity of gas across the open exhaust tube, the flow of gas to atmosphere is increased and therefore $CO_2$ or other gas is reduced at the mask.

Like an earlier embodiment, this system may also provide a means to eliminate excess condensation at a mask when used with a humidifying device.

Triggers Flow Generator

There are benefits of triggering the venting only during the breathing cycle of exhalation. This is one preferred embodiment of the invention. The advantage is that there is a reduced effort on flow generator especially at higher pressures during inhalation when the flow generator has to supply sufficient gas to the patient during highest demand. By reducing leak through the vent at this phase where no $CO_2$ is available to be flushed out, it is desirable to close this intentional leak source off.

This triggering may incorporate electronics or simple mechanical valving, or electro-mechanical valving.

Gas Sampling

Gas sampling of the patient and/or from the mask interface could be provided back at the flow generator. For example, $CO_2$ sensors can monitor whether the $CO_2$ exhaled is excessive and appropriately respond by increasing the vacuum pump speed (to provide less pressure or more flow). The response can be stepped or variable.

Also gas sampling of other breathing gases is possible. For example, where a patient is also receiving Oxygen therapy with their CPAP therapy, the proportion of oxygen and carbon dioxide may be monitored. The machine according to one embodiment of the invention would reduce oxygen delivery where excessive oxygen is sampled on the vacuum side. Also in this example, oxygen, carbon dioxide and treatment pressure can all be monitored and adjusted independently to achieve optimal treatment of the patient by balancing their gas exchange.

Integrated Helical Tubing

The main air delivery tubing and the vacuum tubing in one preferred form of the invention incorporates an integral double-lumen tubing, however combined as a single assembly to minimize bulk in the air tubing. It is preferable to reduce bulk and weight of the air delivery system to maximize comfort to the patient by reducing size and weight. This may be in one form, a vacuum line running around a spiral-like form around the outside of the main air tubing, where the spiral line also forms the structural integrity of the main air tubing to prevent kinking and occlusion.

The above embodiments may result in one or more of the following advantages to the patient:

Greatly improved comfort.
Elimination of air vent noise near patient and bed partner.
Elimination of air jetting onto self or bed partner.
Potentially reduced $CO_2$ rebreathing.
Reduced pressure swings leading to reduced work of breathing and therefore increased comfort to the patient.
Reduced condensation at the mask when used with a humidifier.
The interface or mask system becomes easier to use.
Simplified design leading to easier cleaning and possibly assembly/disassembly.
Ability to tailor the treatment according needs in the more sophisticated embodiments of this invention.

The above embodiments may result in one or more of the following advantages for the physician/clinician:

Potentially longer term patient compliance and acceptance of medical treatment.
Ability to tailor the treatment according needs in the more sophisticated embodiments of this invention. For example increasing pressure swings to reduce $CO_2$ rebreathing.

An intelligent version may be able to modify treatment according to patient needs, for example balancing pressure swings to $CO_2$ rebreathing and varying during the course of treatment.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability to ventilators in general for use with patients and non-patients alike for medical and non-medical applications.

The invention claimed is:

1. A continuous positive airway pressure (CPAP) system comprising:
    a mask adapted to provide CPAP to a patient, the mask including a breathing chamber;
    a flow generator in communication with the mask;
    a positive pressure line to provide positive pressure air from the flow generator to the mask;
    a vacuum or return line provided to actively remove gas exhausted by the patient; and
    a vent outlet in communication with the vacuum or return line to vent the gas exhausted by the patient, the vent outlet provided at a location that is remote from the mask.

2. The CPAP system of claim 1, wherein the mask includes a nozzle assembly including a pair of nozzles provided for respective nares of the patient.

3. The CPAP system of claim 2, wherein at least one of the nozzles includes a dual wall construction including an inner wall and an outer wall defining a substantially annular passage therebetween in communication with the vacuum line.

4. The CPAP system of claim 2, wherein the nozzle assembly includes a first end portion with an elbow in communication with the positive pressure line and a second end portion with an elbow in communication with the vacuum line.

5. The CPAP system of claim 2, wherein the nozzle assembly includes a first end portion that is closed and a second end portion provided with an elbow, the nozzle assembly including a main body having a baffle therein to define a first chamber in communication with the positive pressure line and a second chamber in communication with the vacuum line.

6. The CPAP system of claim 5, wherein the elbow includes at least a portion of each of the positive pressure line and the vacuum line.

7. The CPAP system of claim 5, wherein the baffle is generally planar or a hollow cylinder.

8. The CPAP system of claim 1, wherein the mask includes a port to communicate the passage with the vacuum or return line.

9. The CPAP system of claim 1, wherein the flow generator includes a blower and a vacuum pump.

10. The CPAP system of claim 9, wherein the vacuum pump and the blower comprise separate components.

11. The CPAP system of claim 9, wherein the vacuum pump is integral with the blower.

12. The CPAP system of claim 11, wherein the integral vacuum pump and blower include a motor including first and second shaft ends and respective supply and vacuum impellers provided thereto.

13. A CPAP system of claim 1, further comprising a control member or valve provided to the flow generator in communication with the vacuum or return line, wherein the control member or valve is controlled based on the sensing of at least one of pressure, flow and $CO_2$.

14. The CPAP system of claim 13, wherein the control member or valve is controlled at least in part based on a breathing pattern of the patient, wherein the control member or valve is closed during inhalation and open during exhalation.

15. The CPAP system of claim 1, further comprising a blow-in valve provided to the positive pressure line.

16. The CPAP system of claim 1, further comprising a bypass provided to the vacuum or return line, the bypass having access to a source of pressurized gas which is accelerated via a venturi, to thereby actively draw gas exhaled by the patient along the vacuum or return line.

17. The CPAP system of claim 1, wherein the vacuum line is coupled to a vacuum pump operable at a constant rate.

18. The CPAP system of claim 1, wherein the vacuum line is coupled to a vacuum pump operable at a variable rate.

19. The CPAP system of claim 18, wherein the vacuum pump is operable at two or more speeds based on patient input.

20. The CPAP system of claim 1, wherein flow through of the vacuum or return line is delayed for a predetermined time after sensing a predetermined parameter.

21. The CPAP system of claim 1, wherein the vacuum or return line is in communication with a valve to direct at least a portion of gas to cool a blower within the flow generator.

22. The CPAP system of claim 1, further comprising a vacuum pump provided to the vacuum line, wherein, if or when the vacuum pump is not drawing exhaled gas along the vacuum line, a positive pressure side of the vacuum pump may be diverted back to the positive pressure line to assist with delivering the positive pressure gas to the patient.

23. The CPAP system of claim 1, further comprising a vacuum pump in communication with the vacuum line, the vacuum pump being mounted on the mask.

24. The CPAP system of claim 1, further comprising a vacuum pump in communication with the vacuum line and being controllable to increase negative flow just before and/or during exhalation by the patient.

25. The CPAP system of claim 24, wherein the vacuum pump is controllable to decrease negative pressure and/or increase flow during inhalation of the patient.

26. A CPAP system of claim 1, further comprising means to reduce condensation within the positive pressure line and/or the vacuum line.

27. The CPAP system of claim 26, wherein the means includes heater means that vaporizes or evaporates water in the vacuum line or the positive pressure line.

28. The CPAP system of claim 27, wherein exhausted gas is actively extracted adjacent the mask.

29. The CPAP system of claim 28, wherein the exhausted gas is actively extracted from the breathing chamber.

30. The CPAP system of claim 28, wherein the exhausted gas is actively extracted from an air delivery conduit that communicates the mask and flow generator.

31. The CPAP system of claim 1, wherein the return line is not provided with a negative pressure source.

32. A continuous positive airway pressure (CPAP) system comprising:
    a mask for a patient, the mask including a breathing chamber;
    a flow generator in communication with the mask;
    a positive pressure line to provide positive pressure air from the flow generator to the mask; and
    a vacuum or return line provided to actively extract and/or remove gas exhausted by the patient,
    wherein the positive pressure line includes an air delivery tube, and the vacuum or return line includes a relatively smaller tube which is spirally wound around the perimeter of the air delivery tube.

33. A continuous positive airway pressure (CPAP) system comprising:
    a mark provided for a patient, the mask including a breathing chamber;
    a flow generator in communication with the mask;
    a positive pressure line to provide positive pressure air from the flow generator to the mask; and
    a vacuum or return line provided to actively extract and/or remove gas exhausted by the patient,
    wherein the vacuum or return line is in communication with a vent outlet provided on the flow generator.

34. The CPAP system of claim 33, further comprising a noise reducing device or muffler within the flow generator provided between the vent outlet and the return or vacuum line.

* * * * *